US011998363B2

(12) United States Patent
Chakravarthy et al.

(10) Patent No.: US 11,998,363 B2
(45) Date of Patent: *Jun. 4, 2024

(54) SYSTEM AND METHOD OF PATIENT MONITORING AND SIGNAL QUALITY ANALYSIS

(71) Applicant: Medtronic Monitoring, Inc., San Jose, CA (US)

(72) Inventors: Niranjan Chakravarthy, Singapore (SG); Scott Williams, Shoreview, MN (US); Arthur K. Lai, Minnetonka, MN (US); Brion C. Finlay, Brooklyn Park, MN (US); Rodolphe Katra, Blaine, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/806,344

(22) Filed: Jun. 10, 2022

(65) Prior Publication Data

US 2022/0296170 A1 Sep. 22, 2022

Related U.S. Application Data

(63) Continuation of application No. 16/043,538, filed on Jul. 24, 2018, now Pat. No. 11,357,452.

(51) Int. Cl.
*A61B 5/00* (2006.01)
*A61B 5/259* (2021.01)
*A61B 5/316* (2021.01)

(52) U.S. Cl.
CPC .......... *A61B 5/7221* (2013.01); *A61B 5/0006* (2013.01); *A61B 5/259* (2021.01);
(Continued)

(58) Field of Classification Search
CPC ..... A61B 5/7221; A61B 5/0006; A61B 5/259; A61B 5/316; A61B 5/7203; A61B 5/7264;
(Continued)

(56) References Cited

U.S. PATENT DOCUMENTS 6,603,318 B2 8/2003 Hansen et al.
7,526,345 B2 4/2009 Covey et al.
(Continued)

FOREIGN PATENT DOCUMENTS

WO 2013036718 A1 3/2013
WO WO-2015002945 A2 * 1/2015 ......... A61B 5/02438
(Continued)

OTHER PUBLICATIONS

Notification of Transmittal of the International Search Report and the Written Opinion of the International Searching Authority, or the Declaration for PCT /US2019/036233 dated Aug. 21, 2019.
(Continued)

*Primary Examiner* — Yingchuan Zhang
*Assistant Examiner* — Sebastian X Lukjan
(74) *Attorney, Agent, or Firm* — Shumaker & Sieffert, P.A.

(57) ABSTRACT

A method of determining signal quality in a patient monitoring device includes acquiring one or more signals using the patient monitoring device. One or more signal quality metrics are determined based on the one or more acquired signals. A noise condition is detected based on the one or more signal quality metrics, and a determination is made whether the noise condition should be classified as intermittent or persistent. One or more actions are taken based on the classification of detected noise as intermittent or persistent.

20 Claims, 19 Drawing Sheets

(52) U.S. Cl.
CPC ............ *A61B 5/316* (2021.01); *A61B 5/7203* (2013.01); *A61B 5/7264* (2013.01); *A61B 5/746* (2013.01); *A61B 2560/0271* (2013.01); *A61B 2560/0276* (2013.01); *A61B 2562/0219* (2013.01)

(58) Field of Classification Search
CPC ............ A61B 5/746; A61B 2560/0271; A61B 2560/0276; A61B 2562/0219; A61B 5/6832; A61B 5/742; A61B 5/02438; A61B 5/02455; A61B 5/318; A61B 5/6802

See application file for complete search history.

(56) References Cited

U.S. PATENT DOCUMENTS

| | | |
|---|---|---|
| 8,005,552 B2 | 8/2011 | Covey et al. |
| 8,116,864 B2 | 2/2012 | Covey et al. |
| 8,185,191 B1 | 5/2012 | Shapiro et al. |
| 8,805,482 B2 | 8/2014 | Sitzman et al. |
| 9,026,198 B2 | 5/2015 | Lian et al. |
| 9,724,008 B2 | 8/2017 | Sullivan et al. |
| 11,357,452 B2 * | 6/2022 | Chakravarthy ........ A61B 5/318 |
| 2004/0015197 A1 | 1/2004 | Gunderson |
| 2004/0228217 A1 | 11/2004 | Szeto |
| 2010/0022903 A1 | 1/2010 | Sitzman et al. |
| 2016/0000349 A1 | 1/2016 | Sullivan et al. |
| 2017/0367600 A1 | 12/2017 | Pemberton et al. |
| 2018/0075861 A1 | 3/2018 | Ukil et al. |
| 2018/0085022 A1 | 3/2018 | Katra et al. |
| 2018/0206752 A1 * | 7/2018 | Bardy .................... A61B 5/363 |
| 2019/0030352 A1 * | 1/2019 | Sullivan ............... A61N 1/3987 |
| 2019/0298210 A1 * | 10/2019 | Bennet ................ A61B 5/0245 |

FOREIGN PATENT DOCUMENTS

| | | |
|---|---|---|
| WO | 2016198288 | 12/2016 |
| WO | 2017033140 A1 | 3/2017 |
| WO | 2017174738 | 10/2017 |
| WO | 2017222888 A1 | 12/2017 |

OTHER PUBLICATIONS

Prosecution History from U.S. Appl. No. 16/043,538, dated Apr. 24, 2020 through Feb. 15, 2022, 140 pp.

First Office Action and Search Report, and translation thereof, from counterpart Chinese Application No. 201980049217.2 dated Nov. 28, 2023, 17 pp.

* cited by examiner (Patient A)

(Patient B)

(Patient C)

(Patient B)

(Patient C)

(Patient A)

(Patient D)

(Patient A)

(Patient B)

(Patient C)

(Patient D)

SYSTEM AND METHOD OF PATIENT MONITORING AND SIGNAL QUALITY ANALYSIS

RELATED APPLICATION

This application is a Continuation of U.S. application Ser. No. 16/043,538, filed Jul. 24, 2018, the entire content of which is incorporated herein by reference.

TECHNICAL FIELD

The invention relates generally to patient monitoring devices, and, in particular, to a system and method for determining signal quality of the patient monitoring device.

BACKGROUND

Monitoring devices have become increasingly prevalent in long-term patient monitoring. For example, insertable devices, adherent devices and/or Holter-type devices may be utilized to collect one or more of electrocardiogram (ECG) data, bio-impedance data, accelerometer data, and other physiological data. Signal quality monitoring is an important aspect to long-term patient monitoring for a number of reasons.

In some applications, a monitoring device is attached to a patient and collects data for a prescribed period of time. At the end of the monitoring period, the data is analyzed and typically a portion of the data is determined to be too noisy to utilize. In other applications, the monitoring device detects conditions in the monitored signals and communicates those signals determined to be indicative of a serious problem to a monitoring center for review. However, the presence of noise in the monitored signal may result in false alarms being communicated to the monitoring center, each of which must be reviewed. In each case, it would be beneficial to be able to determine signal quality during the monitoring period and take action to remedy if needed.

SUMMARY

A method of determining signal quality in a patient monitoring device includes acquiring one or more signals using the patient monitoring device. One or more signal quality metrics are determined based on the one or more acquired signals. A noise condition is detected based on the one or more signal quality metrics, and a determination is made whether the noise condition should be classified as intermittent or persistent. One or more actions are taken based on the classification of detected noise as intermittent or persistent.

DETAILED DESCRIPTION

The present disclosure provides a system and method of monitoring physiological parameters of a patient and during the monitoring period, extracting a number of signal quality metrics from the monitored signals, and utilizing the signal quality metrics to determine the quality of the signal monitored (e.g., noisy or non-noisy). In this way, signal quality is determined based on the interpretability and quality of the signal being measured. This is in contrast with prior art systems, which rely only on measures of electrical contact and mechanical adhesion, and which fail to make determinations regarding the quality of the signal data being acquired.

Figure 1:
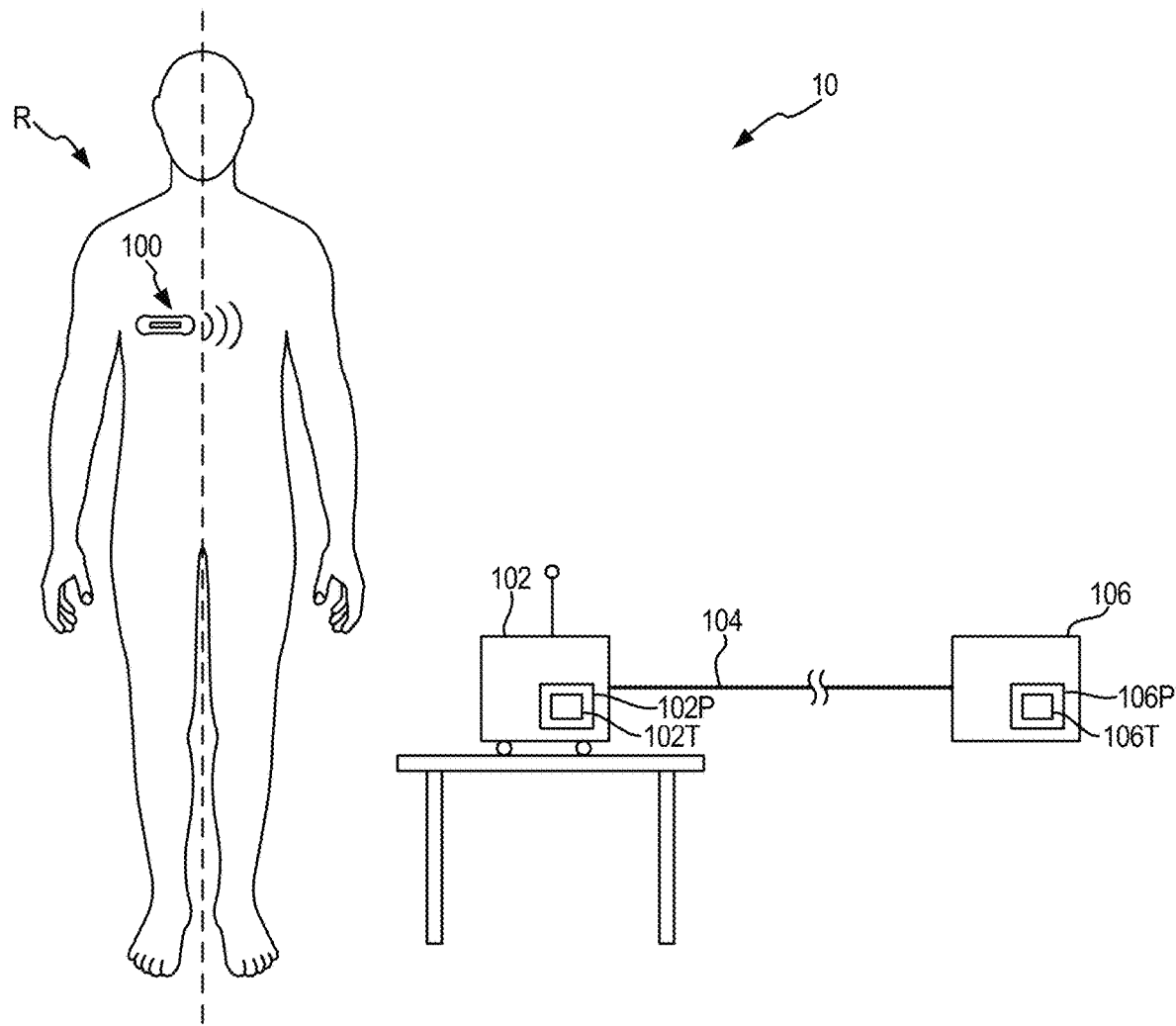
FIG. 1 is a simple diagram of a patient monitoring system according to some embodiments.

FIG. 1 shows a patient P and a monitoring system 10. Monitoring system 10 comprises a patient measurement device 100, gateway 102, and remote monitoring center 106. In the embodiment shown in FIG. 1, patient measurement device 100 is an adherent device that attaches to the skin of the patient, but in other embodiments may be an implantable or injectable device. In some embodiments the patient measurement device 100 is a Holter-type monitoring device that records data but does not communicate in real-time to either gateway 102 and/or remote monitoring center 106. Patient monitoring device 100 can be adhered, attached and/or injected to a patient P at many locations, for example thorax T of patient P. A benefit of utilizing an adherent, injectable, and/or implantable device is that it may be utilized to collect physiological data from the patient while the patient goes about normal day-to-day activities outside of a hospital setting.

Patient measurement device 100 includes a plurality of different types of sensors that are capable of monitoring a variety of different types of attributes, including one or more of electrocardiogram sensors, bioimpedance sensors, accelerometer sensors, optical sensors, etc. For example, the electrocardiogram sensor may be comprised of first and second electrodes and electrocardiogram sensing circuitry. For example, in an adherent device the first and second electrodes may be conductively couple to the skin of the patient P via a conductive hydrogel to sense electrocardiogram signals. In an insertable and/or implantable devices, two or more electrodes may be located in contact with patient tissue to sense electrocardiogram signals. Similarly, the patient measurement device 100 may include two or more electrodes and bioimpedance circuitry utilized to measure bioimpedance of the surrounding tissue. For example, in an adherent device the bioimpedance sensor may include two or more (e.g., four) electrodes conductively coupled via hydrogel to the skin of the patient. In some embodiments, the bioimpedance circuitry forces a current at one or more frequencies between two of the electrodes and monitors the voltage between two additional electrodes in order to determine the impedance associated with the tissue. In some embodiments, the accelerometer is a three-axis accelerometer that monitors acceleration in three axis, which can be utilized to determine activity and/or orientation of the patient. From the sensed signals, a plurality of physiological parameters can be monitored. For example, in some embodiments, the plurality of sensors are utilized to monitor a variety of different types of data, including one or more of electro-cardiogram signals (ECG), bio-impedance, respiration, heart rate, heart rhythm, heart rate variability (HRV), heart rate turbulence (HRT), heart sounds, respiratory sounds, blood pressure, activity (e.g., rest, active), posture, and wake/sleep. In one embodiment, ECG signals are utilized to automatically detect arrhythmic states. As described in more detail below, additional physiological parameters are measured/monitored by patient monitoring device 100 and utilized either alone or in combination to make determinations regarding patient state (e.g., patient motion may be monitored to determine an activity level of the patient). However, the value of determined patient status is a function of the signal quality associated with the underlying measurements. If the data signal is very noisy, then the determination of patient status (e.g., arrhythmic, etc.) may be incorrect. Determining the quality and interpretability of the monitored signals improves the reliability associated with algorithmic diagnosis of conditions (e.g., arrhythmias, etc.).

In some embodiments, patient monitoring device 100 can wirelessly communicate with remote center 106. The communication may occur directly (via a cellular or Wi-Fi network), or indirectly through intermediate device or gateway 102. The gateway 102 may comprise components of the zLink™, a small portable device similar to a cell phone that wirelessly transmits information received from patient monitoring device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by expert human operators to verify accuracy. For example, ECG strips captured and communicated to remote center 106 from adherent device 100 can be adjudicated for arrhythmias by experts located at remote center 106. Communication may include physiological data monitored by adherent device 100 or may include analysis/reports generated locally by adherent device 100.

In some embodiments, data is communicated in real-time or near real-time to either the gateway 102 and/or the remote center 106 for analysis. In other embodiments, data is merely collected by the patient monitoring device. For example, a Holter monitor is utilized to collect data for the duration of the monitoring period. At the conclusion of the monitoring period, collected data is provided to monitoring center 106 for review and analysis.

Regardless of whether data is communicated in real-time or near real-time to gateway 102 and/or remote monitoring center 106 or whether data is merely collected during the monitoring period for subsequent review and analysis, it is beneficial to make determinations regarding the quality of the signals being monitored and/or recorded. For example, in one embodiment a determination of poor signal quality may result in a notification to the patient to reposition the patient monitoring device 100 and/or replace the patient monitoring device 100 (to the extent possible).

In some embodiments, monitoring system 10 comprises a distributed processor system with at least one processing module (not shown) included as part of patient monitoring device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters monitored by adherent device 100 may be analyzed by one or more of the distributed processors included as part of patient monitoring device 100, gateway 102, and/or remote monitoring center 106. Signal quality determinations may be made by one or more of the distributed processors included as part of patient monitoring device 100, gateway 102, and/or remote monitoring center 106.

In some embodiments, patient monitoring device 100 may continuously monitor physiological parameters, record monitored physiological parameters, communicate wirelessly with a remote center, and/or provide alerts when necessary. The patient monitoring device may attach or be otherwise affixed to the patient's thorax and contain sensing electrodes, battery, memory, logic, and wireless communication capabilities. In some embodiments, patient monitoring device 100 locally monitors signal quality associated with the monitored physiological parameters. Signal quality may be monitored locally regardless of whether data is merely collected by the patient monitoring device 100 or collected and analyzed by patient monitoring device.

Based on the determined signal quality, a number of different actions may be taken, and those actions may be dictated by the determined cause of the presumably poor signal quality. In some embodiments, noisy signal quality is classified as either intermittently noisy or persistently noisy. Whether the signal quality is classified as intermittently noisy or persistently noisy may affect the response initiated. For example, in some embodiments if the signal quality is determined to be intermittently noisy, flags/notifications are set that indicate to downstream algorithms that signal quality is intermittently noisy. In response, downstream algorithms may take one or more actions, from disregarding the intermittently noisy data, to de-emphasizing the conclusions drawn from the data, to weighting the results of the data analysis differently. In addition, a determination that the data signal is intermittently noisy may result in some action to remedy the noisy condition. For example, this may include generating an alert that is provided to one or more of the patient P, the physician, the technician, or the remote monitoring center indicating the intermittent noise condition. This may include simply alerting the patient of the condition, and/or prompting the user to take some action to remedy the signal quality issue. In some embodiments, if the signal quality is determined to be persistently noisy, then the collection and/or processing of signal data may be suspended until the determined signal quality improves. In some embodiments, a persistent noise condition indicates that the patient monitoring device has been removed and/or needs to be replaced. For example, in embodiments utilizing an adhesive patient monitoring device, a determination of persistent noise indicates expiration/deterioration of the hydrogel portions relied upon to make electrical contact between the skin of the patient P and the electrodes of the adherent patch. In this example, the patient P may be prompted to replace the old adhesive patch with a new adhesive patch. In addition, in some embodiments an alert or notification may be generated instructing the patient to replace the patient monitoring device (or in some embodiments, to continue wearing the monitoring device). In some embodiments, a notification may be provided to the remote monitoring center, which may then follow-up with the patient to ensure compliance during the monitoring period.

In some embodiments, signal quality metrics include both ECG signal-based quality metrics and those based on device electrical design and other sensors. The ECG signal-based quality metrics include one or more of beat noise flags, ECG flatline detection, and deviation in QRS height and detected heart rate. Those based on device electrical design and other sensors include one or more of V+/V− integrity flags, device detach flags, bioimpedance metrics, and accelerometer metrics. As described in more detail below, these signal quality metrics are utilized alone or in combination with one another to make determinations regarding the signal quality of monitored physiological signals. In some embodiments, signal quality at the start of patient monitoring may rely on one or more different signal quality metrics than those utilized during patient monitoring.

Figure 2:
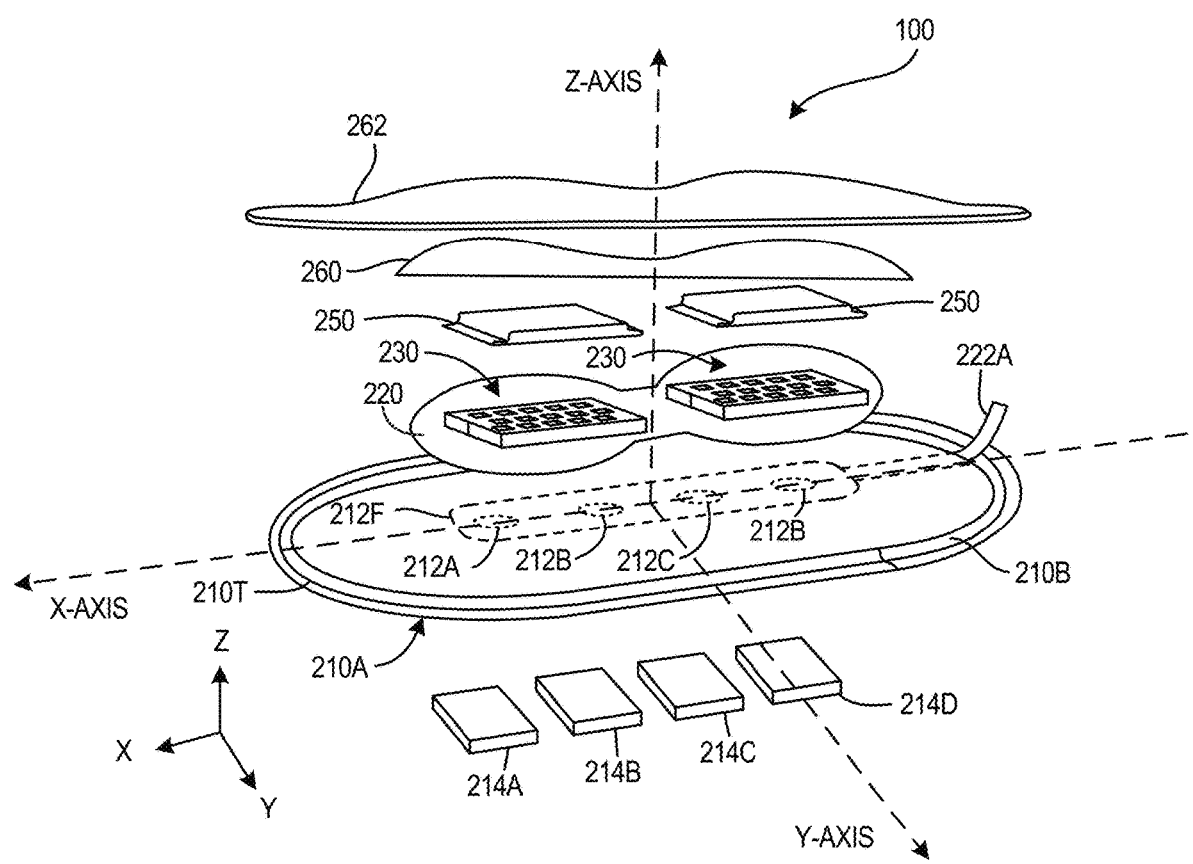
FIG. 2 is an exploded view of a type of patient monitoring device utilized according to some embodiments.

FIG. 2 is an exploded view of a patient monitoring device 200 that may be utilized according to some embodiments. In the embodiment shown in FIG. 2, patient monitoring device is an adherent device attached to the skin of the patient P. Adherent device 200 includes adherent tape 210T, two or more electrodes 212A, 212B, 212C, 212D with gels 214A, 214B, 214C, 214D, printed circuit board (PCB) 220, flexible connected 222A, electrical components/sensors 230 mounted on PCB 220, batteries 250, electronics housing cover 260, and flexible cover 262.

Adherent device 200 comprises at least two electrodes—although the embodiment shown in FIG. 2 includes electrodes 212A, 212B, 212C and 212D. Adherent device 200 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 200 comprises a first side, or a lower side 210A, that is oriented toward the skin of the patient when placed on the patient. The adherent patch 200 may also comprise a tape 210T which is a material, preferably breathable, with an adhesive (not shown) to adhere to patient P. Electrodes 212A, 212B, 212C and 212D are affixed to adherent patch 200. In many embodiments, at least four electrodes are attached to the patch. Gels 214A, 214B, 214C and 214D can each be positioned over electrodes 212A, 212B, 212C and 212D, respectively, to provide electrical conductivity between the electrodes and the skin of the patient. As discussed above, expiration/deterioration of gels 214A, 214B, 214C and 214D may result in persistent noise conditions despite good mechanical contact between the adherent patch 200 and patient P.

Adherent patch 200 also comprises a second side, or upper side 210B. In many embodiments, electrodes 212A, 212B, 212C and 212D extend from lower side 210A through adherent patch 200 to upper side 210B. An adhesive can be applied to upper side 210B to adhere structures, for example a breathable cover, to the patch such that the patch can support the electronics and other structures when the patch is adhered to the patient. In many embodiments, adherent patch 200 may comprise a layer of breathable tape 210T, for example a tricot-knit polyester fabric, to allow moisture vapor and air to circulate to and from the skin of the patient through the tape. Electrical signals received at electrodes 212A-212D may be communicated to electronic components 230 via flexible connection 222A, which is connected to PCB 220. Electronic components 230 may include a combination of hardware (e.g., analog components), firmware (e.g., field-programmable gate arrays (FPGA)), and/or software running on a microprocessor, utilized to filter, condition, convert to digital, analyze, and/or store signal data.

In some embodiments, electronic components 230 may include ECG circuitry utilized to generate electrocardiogram signals and data from two or more of electrodes 212A, 212B, 212C and 212D in many ways. In some embodiments, ECG circuitry (not shown) is connected to inner electrodes 212B and 212C, which may comprise sense electrodes of the impedance circuitry as described above. In many embodiments, the ECG circuitry may measure the ECG signal from electrodes 212A and 212D when current is not passed through electrodes 212A and 212D. In some embodiments, electronic components 230 may include additional circuitry for monitoring the bioimpedance of tissue adjacent to the two or more electrodes. In some embodiments, bioimpedance circuitry includes circuitry for supplying/injecting a current between at least two of the electrodes (for example, between electrodes 212A and 212D). In response to the injected current, a voltage is measured between two of the electrodes (for example, electrodes 212B and 212C) to determine the impedance associated with adjacent tissue.

In addition, electronic circuitry 230 may comprise a processor module that can be configured to analyze physiological parameters monitored by adherent device 200 and to control collection and transmission of data from the electrocardiogram circuitry. In one embodiment, the processor module included as part of electronic circuitry 230 comprises a tangible medium, for example read only memory (ROM), electrically erasable programmable read only memory (EEPROM) and/or random access memory (RAM). Processing of monitored physiological parameters such as ECG signals, bioimpedance signals, etc. may therefore be distributed between the local processor module included as part of electronic circuitry 230 and remote monitoring system 106.

In some embodiments, electronic circuitry 230—including the processor module—are utilized to measure one or more signal quality measurements. In some embodiments, signal quality measurements includes one or both of ECG signal-based quality measurements and those based on device electrical design and/or other sensors. As described above, the ECG signal-based quality metrics include one or more of beat noise flags, ECG flatline detection, and deviation in QRS height and detected heart rate (HR). In some embodiments, the ECG circuitry utilized to process the ECG signal is utilized to measured ECG signal-based quality metrics. The signal-quality measurements based on device electrical design and other sensors include one or more of V+/V− integrity flags, device detach flags, bioimpedance metrics, and accelerometer metrics.

In many embodiments, electronics components 230 comprise wireless communications circuitry (not shown) to communicate with remote center 106. PCB 220 may comprise an antenna to facilitate wireless communication. The antenna may be integral with PCB 220 or may be separately coupled thereto. The wireless communication circuitry can be coupled to the impedance circuitry, the electrocardiogram circuitry and the accelerometer to transmit to a remote center with a communication protocol the monitored data signals. In specific embodiments, the wireless communication circuitry is configured to transmit collected data signals to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two way protocol such that the remote center is capable of issuing commands to control data collection.

Figure 3:
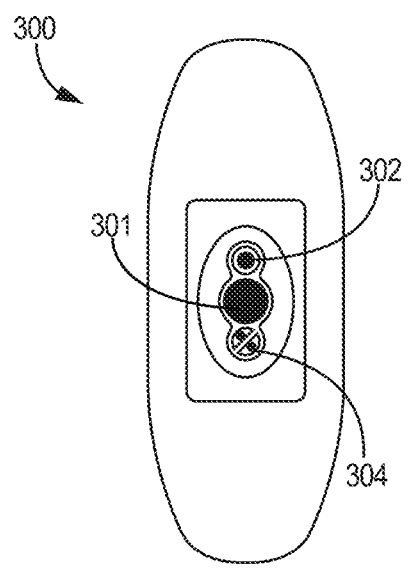
FIG. 3 is a top view of a type of patient monitoring device utilized according to some embodiments.

FIG. 3 is a top view of adherent device 300 according to some embodiments. Adherent device 300 includes activation button 301, first alert 302 and second alert 304. Activation button 301 can be activated by a patient in response to symptoms felt by the patient in order to ensure that data is recorded and/or communicated to a monitoring center. First alert 302 provides an indication to the patient P of the operating status of the adherent device (e.g., intermittent noise, good quality). In some embodiments, first alert 302 is a light providing a first color (e.g., green) when signal quality is good and a second color (e.g., red) when signal quality is noisy. In response to the first alert 302 indicating that the signal quality is noisy, the patient P may be prompted to modify the position of adherent device 300 and/or reduce motion/physical activity to reduce noise associated with the adherent device. For example, first alert 302 may be utilized when applying the adherent device to ensure that the device is adhered to the patient correctly and signal quality is good. In the event that the first alert 302 indicates that the signal quality is intermittently noisy, the patient P may be prompted to modify the position of the sensor, and/or refrain from physical activity for several minutes in order to determine whether signal quality can be determined. In many instances, this step occurs while the patient is under the supervision of a technician and/or doctor to ensure the device is operating properly before the patient leaves the facility.

In contrast, in some embodiments second alert 304 provides an alert that indicates a persistent noise condition. In some embodiments, this may be an indication that the patient P needs to take action in replacing at least a portion of the adherent device 300. For example, in some embodiments adherent device 300 includes a reusable portion and a disposable portion. In response to activation of second alert 304, the patent P removes a first disposable portion and attaches a second (e.g., new) disposable portion. In this way, first and second alerts 302 and 304 provide a way of communicating signal quality issues to the patient P, and furthermore allow different types of signal quality issues (e.g., intermittent noise versus persistent noise) to be communicated to the user.

ECG-Based Signal Quality Measurements

As discussed above, ECG-based signal quality measurements include one or more of noise detection based on beat noise flags, flatline noise detection, and noise detection via QRS height and HR deviation.

Figure 4A:
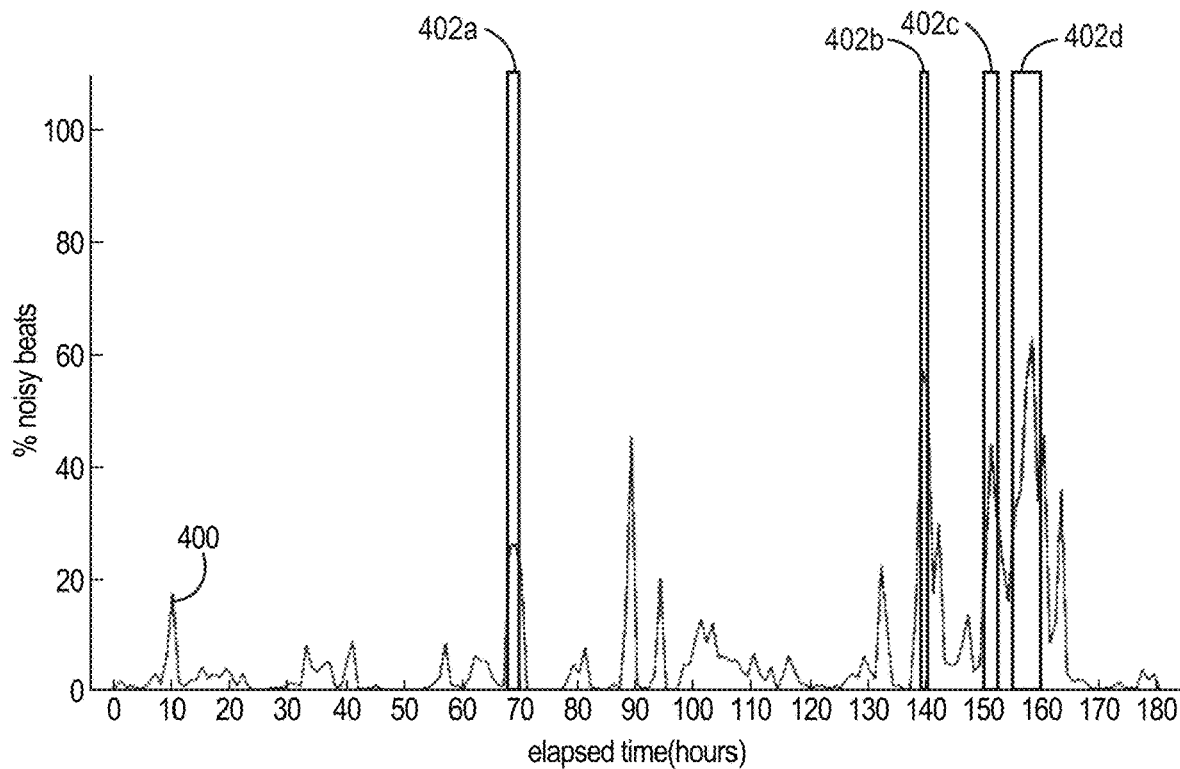
FIGS. 4a-4c are graphs illustrating how noisy beats are utilized determine signal quality according to some embodiments.
Figure 4B:
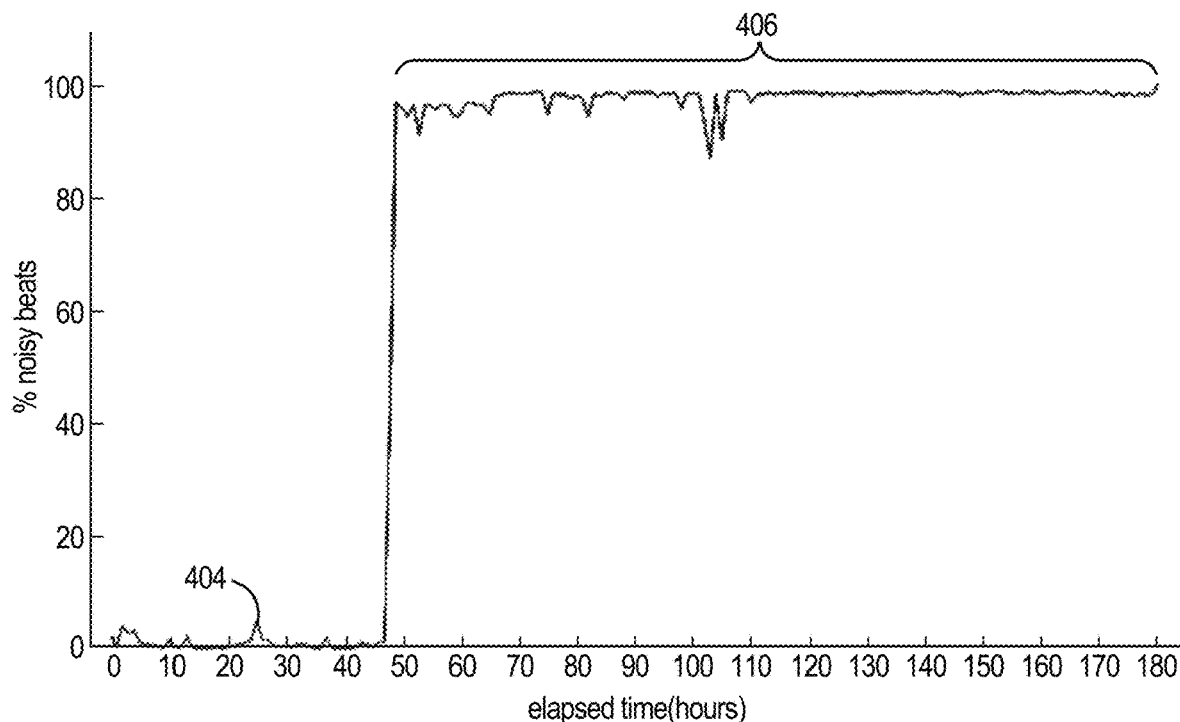
Figure 4C:
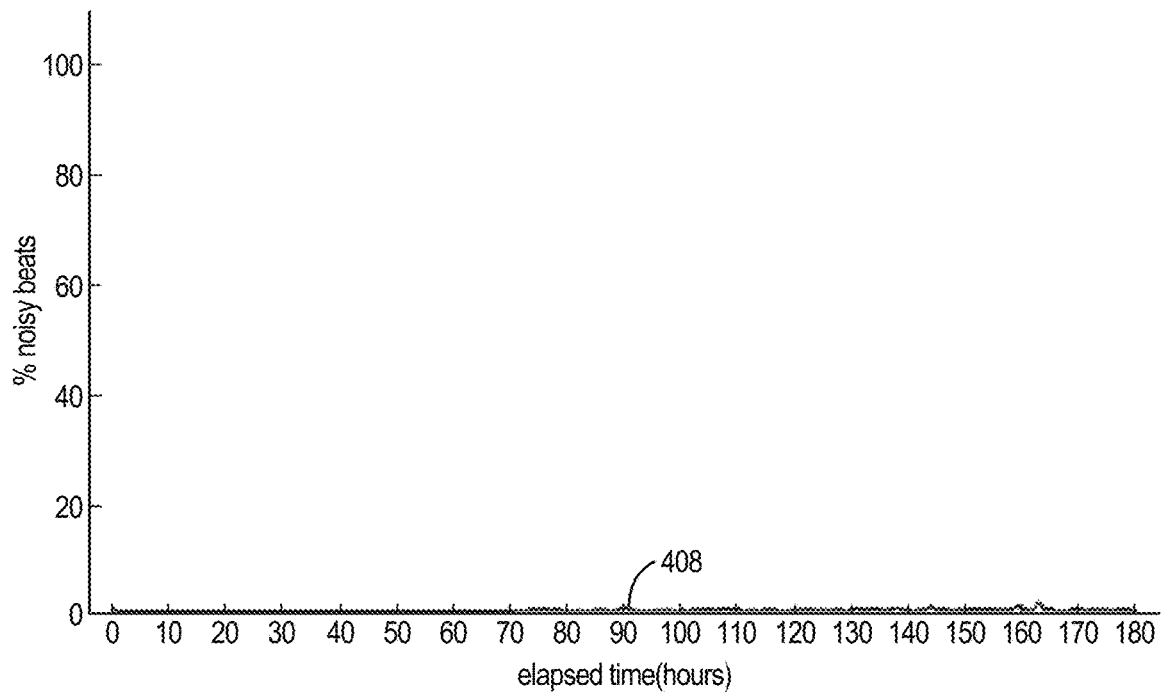

FIGS. 4a-4c are graphs illustrating how the percentage of noisy beats detected in the monitored ECG signal can be utilized to distinguish between intermittent noise states, persistent noise states and normal monitoring, respectively. In some embodiments, beat noise flags refer to analysis of the monitored ECG signal for the presence of high-frequency noise (e.g., muscle-induced artifacts), ECG signal clipping noise, electrode motion noise, low-amplitude QRS noise, and/or spike noise. If any of these noise elements are detected, the beat is noisy and is identified with a beat noise flag. As discussed in more detail below, noisy beats are expected in response to patient movement, intermittent interference, etc. However, if the percentage of noisy beats remains persistently high, this is an indication of poor electrical contact or device removal. For example, FIGS. 4a and 4b are graphs illustrating a percentage of noisy beats detected over the monitoring period (approximately 180 hours), with lines 400 and 404 illustrating the percentage of noisy beats detected, respectively. In the example shown in FIG. 4a, patient movement results in intermittent increases in the percentage of noisy beats as indicated by regions 402a, 402b, 402c, and 402c. For example, between approximately 150-160 hours, a relatively high percentage of noisy beats are detected, but the detection is intermittent, and thus likely a result of patient movement. While the data collected during the intermittent noise period is likely not useful for making determination regarding patient state, it does not indicate a condition in which the device needs to be replaced, or otherwise repositioned (e.g., does not indicate a persistent noise state). In some embodiments, an alert may be generated (e.g., using one of the alerts associated with the adherent device), indicating to the patient P the intermittent noise condition. In response, the patient P may limit movement or may check to ensure that the signal quality problems do not persist for a long period of time.

In contrast with the intermittent noise detected in FIG. 4a, the example shown in FIG. 4b illustrates the detection of a persistent noise state. In this example, the percentage of noisy beats is relatively low until approximately 45-50 hours, at which point the percentage of noisy beats becomes persistently high and remains so for the duration of the monitoring period as indicated by bracket 406. In some embodiments, the percentage of noisy beats (e.g., number of noisy beats to non-noisy beats) as well as the duration of noisy beats is utilized to detect a persistent noise state. This may be caused by detachment of the device or poor electrical contact of the device with the patient. In some embodiments, an alert may be generated, indicating to one or more of the patient P, the physician, the technician, and/or the remote monitoring center 106 that the signal quality is persistently noisy. In some embodiments, in response to a detected persistent noise state, actions are taken to ensure the patient is wearing the patient medical device and/or to prompt the user to replace the disposable portion with a new disposable portion.

FIG. 4c illustrates an embodiment in which neither intermittent nor persistent noise beats are detected, as indicated by the relatively low percentage of noise beats throughout the monitoring period as indicated by line 408. In this example, no alert would be generated at any time—either intermittent or persistent, and normal processing of the monitored data signals would continue.

Figure 5:
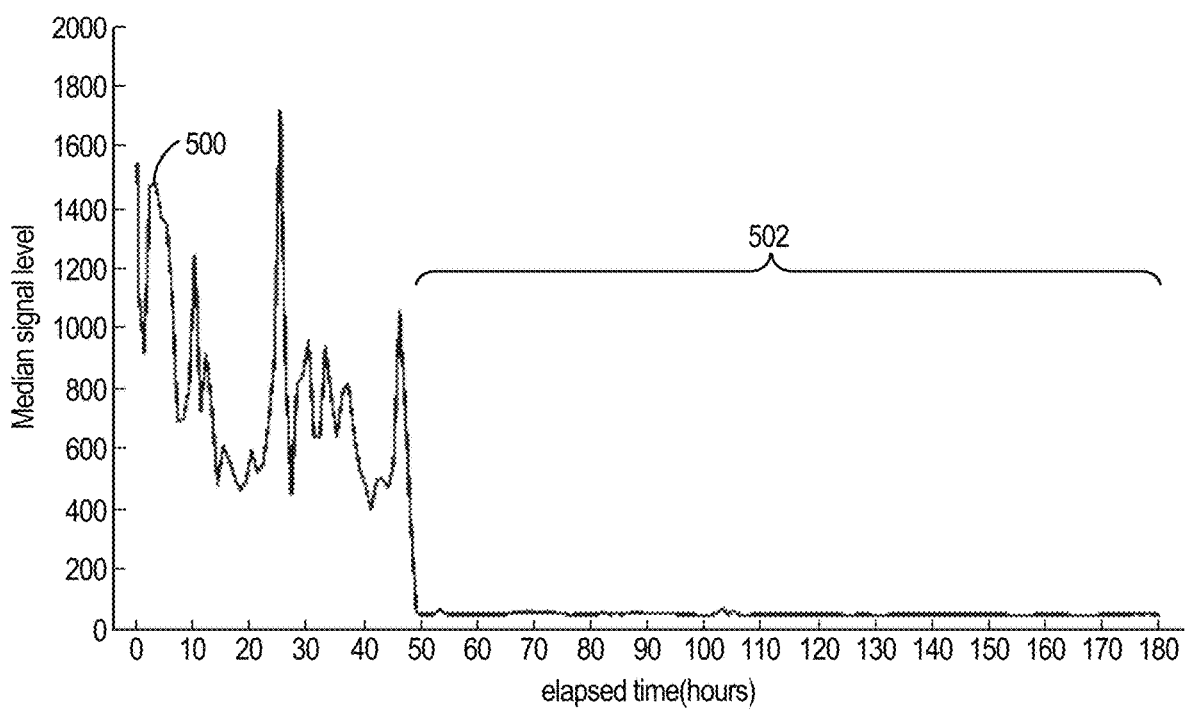
FIG. 5 is a graph illustrating how ECG flatline detection is utilized to determine signal quality according to some embodiments.

FIG. 5 is a graph illustrating how ECG flatline detection bin the monitored ECG signal can be utilized to detect noise states. In particular, when a monitoring device (e.g., adherent device) is removed from the body, the ECG signal typically saturates and is seen as a "flat line". In some embodiments, this condition is detected by monitoring the median signal level associated with the ECG. For example, FIG. 5 illustrates the median ECG signal level (line 500) over a period of 180 hours. Until approximately 50 hours into the monitoring period, the median ECG signal level varies regularly. At approximately 50 hours, the median ECG signal level falls dramatically and remains flatlined for the remainder of the monitoring period, as indicated by bracket 502. This is indicative of a persistent noise state (e.g., device has been completely removed from the patient's body). In response, an alert may be generated (e.g., activation of first or second alerts 302 and 304 on the device itself) or a notification may be communicated to the patient and/or monitoring physician regarding the removal of the device. In this way, the median ECG signal level is utilized to detect persistent noise states resulting from total detachment of the device.

Figure 6A:
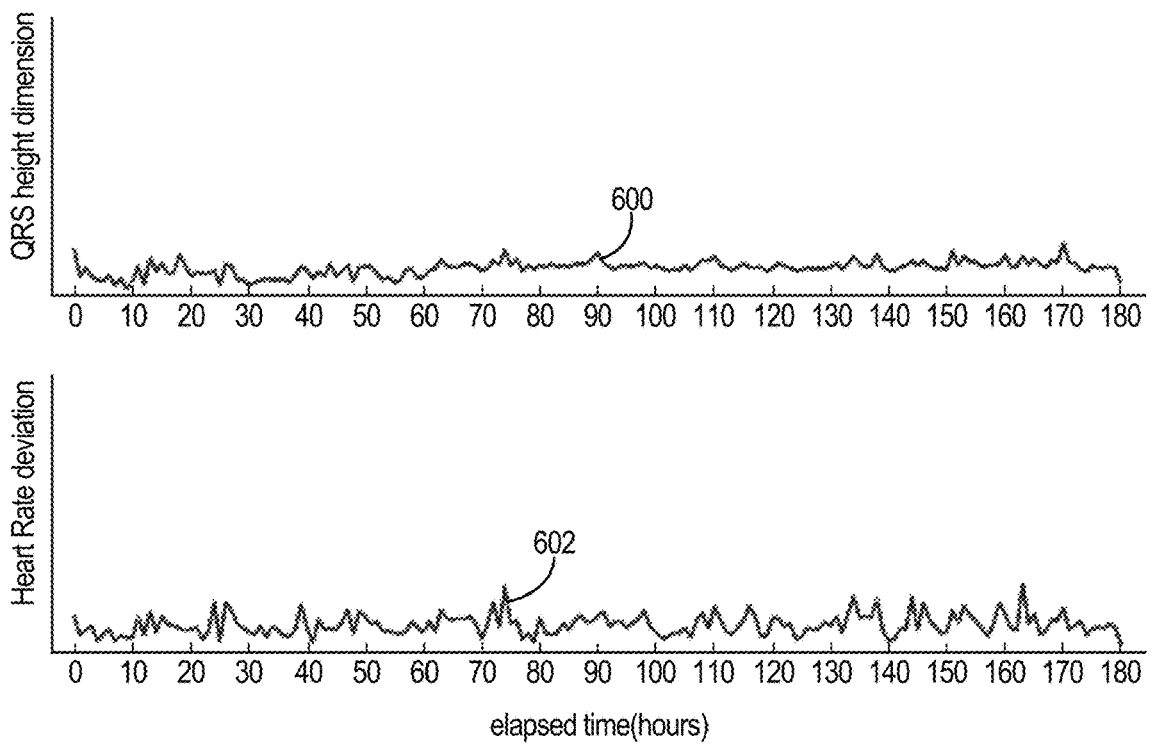
FIGS. 6a-6c are graphs illustrating how QRS height deviation and detected heart rate deviation are utilized to determine signal quality according to some embodiments.
Figure 6B:
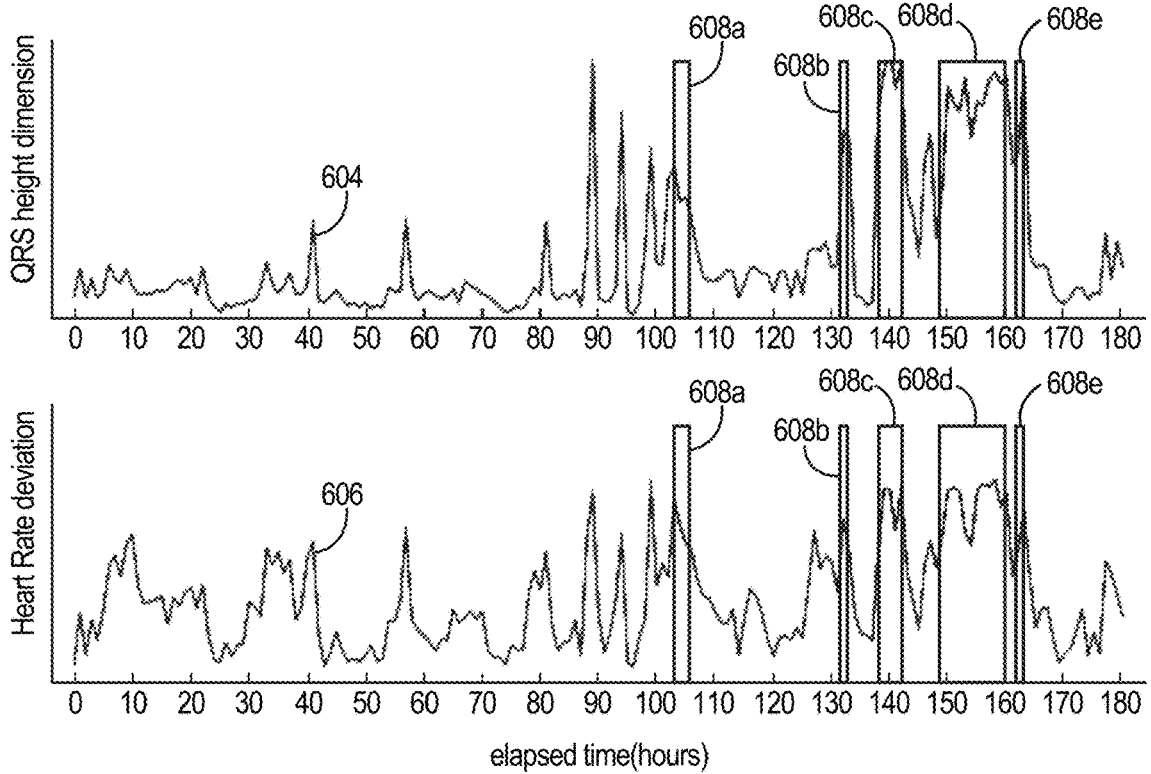
Figure 6C:
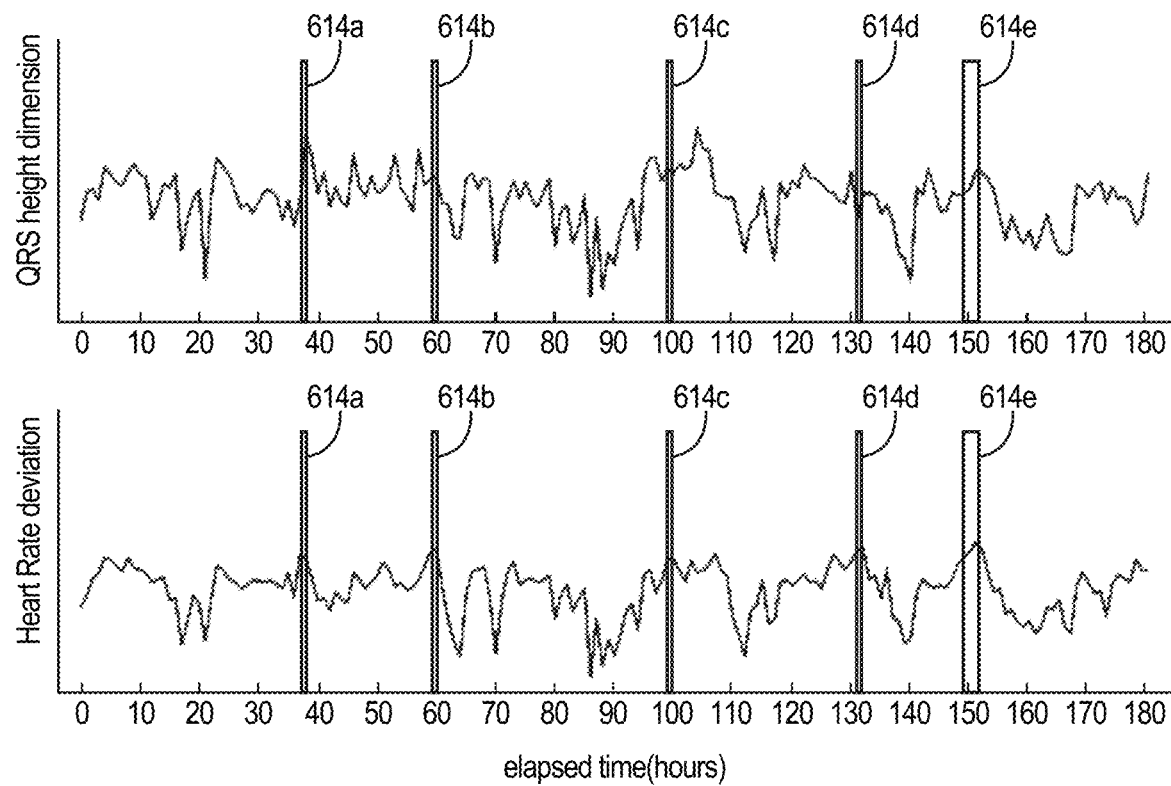

FIGS. 6a-6c are graphs illustrating how QRS height deviation and detected heart rate (HR) deviation from average values can be utilized to detect noise conditions. As part of the ECG monitoring, ECG beats are continuously detected in the ECG signal. Durations of noise and/or artifacts are typically reflected in large QRS height deviations in combination with a very large HR deviation. In some embodiments, HR deviation can be expected throughout the day depending on the activity level of the patient and whether the patient is in a rest state or not. However, if both the QRS height and HR experience large deviations at approximately the same time, this is indicative of a noisy signal.

The embodiment shown in FIG. 6a illustrates an example in which both deviations in both QRS height (top graph, line 600) and heart rate (bottom graph, line 602) are very low over the duration of the monitoring period. As a result, neither an intermittent nor persistent noise state is detected, and normal monitoring proceeds for the duration of the monitoring period.

In contrast, the example shown in FIG. 6b illustrates deviations in both QRS height (top graph, line 604) and heart rate (bottom graph, line 606) that include large intermittent deviations at approximately the same time. In this embodiment, signal quality is determined to be noisy when both QRS deviations 604 and heart rate deviations 606 exceed threshold values. In the embodiment shown in FIG. 6b, this condition is satisfied at times 608a, 608b, 608c, 608d, and 608e. In some cases, QRS deviation may exceed the threshold while the HR deviation does not, and vice versa, such that no noise condition is detected. In the embodiment shown in FIG. 6b, the periods of time in which both QRS deviations 604 and HR deviations 606 exceed thresholds (as indicated by time periods 602a-602e) are intermittent in nature, indicating that the noise condition is an intermittent one and not a persistent one.

The example shown in FIG. 6c illustrates deviations in both QRS height (top graph, line 610) and HR (bottom graph, line 612), but in response to an underlying physiological condition, in this case, an arrhythmia, which causes the patient's heart rate (HR) to increase. In this example, there are five periods of time, labeled 614a, 614b, 614c, 614d, and 614e, in which deviations in both QRS height and HR are intermittently high, indicating a noise condition. In this example, the extremely intermittent nature of the deviations can be utilized to determine that the underlying condition is physiological (e.g., arrhythmia) rather than noise. In addition, one or more other signal quality metrics may be utilized to verify that the detected deviations in QRS height and HR are a result of underlying physiological condition rather than noise. For example, percentage of noisy beats (shown in FIGS. 4a-4c) and/or median ECG signal level (shown in FIG. 5) may be utilized to verify that the QRS height and HR deviations are physiological.

Signal Quality Based on Device Electrical Design and Other Sensors

In addition to analyzing the ECG signal itself to determine signal quality, other aspects of the sensors may be analyzed to detect signal quality, including one or more of V+/V− integrity flags, device detach flags, bioimpedance signals, and accelerometer signals.

FIGS. 7a-7d illustrates embodiments in which the V+/V− integrity is monitored to detect signal quality. In some embodiments, the monitoring device includes at least two electrodes (e.g., electrodes 212a, 212b, 212c, and 212d shown in FIG. 2), any two of which may be referred to as the V+/V− electrodes. The voltage at any one of these electrodes may be monitored with respect to a reference voltage (e.g., body reference value), which is reflected in a V+ or V− to reference signal 700, 702, 704 and 706 illustrated in FIGS. 7a-7d, respectively. The V+/V− integrity flag is turned On (i.e., onset) in response to the V+ or V− connection being compromised, and the flag is turned Off (i.e., offset) in response to both connections being established.

Figure 7A:
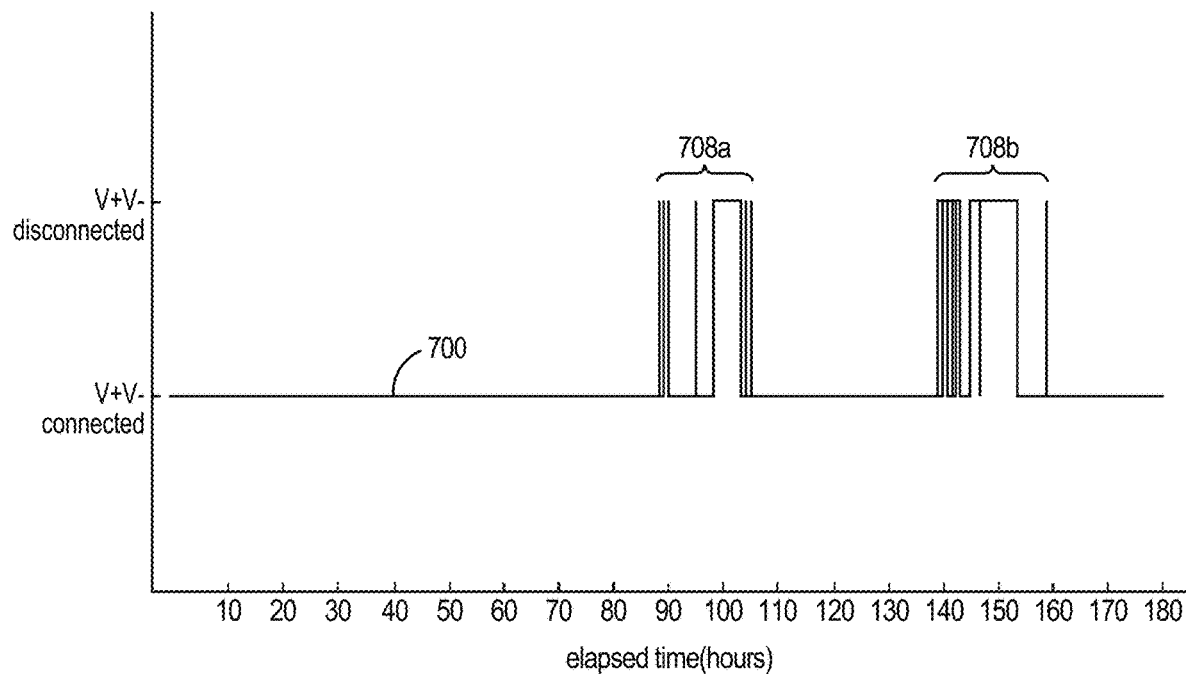
FIGS. 7a-7d are graphs illustrating how V+/V− integrity is utilized to determine signal quality according to some embodiments.

With respect to the example shown in FIG. 7a, the V+/V− integrity flag is intermittently onset and offset over the course of wear during time periods 708a and 708b, indicating a possible noisy condition due to intermittent electrical connection issues (i.e., intermittent noise). As discussed above, in response to intermittent noise, flags/notifications may be generated to deemphasize signals monitored during periods of intermittent noise. In addition, alerts/notifications may be generated with respect to the patient P, physicians, technicians, remote monitoring center 106, etc., to alert them to the intermittent noise condition.

Figure 7B:
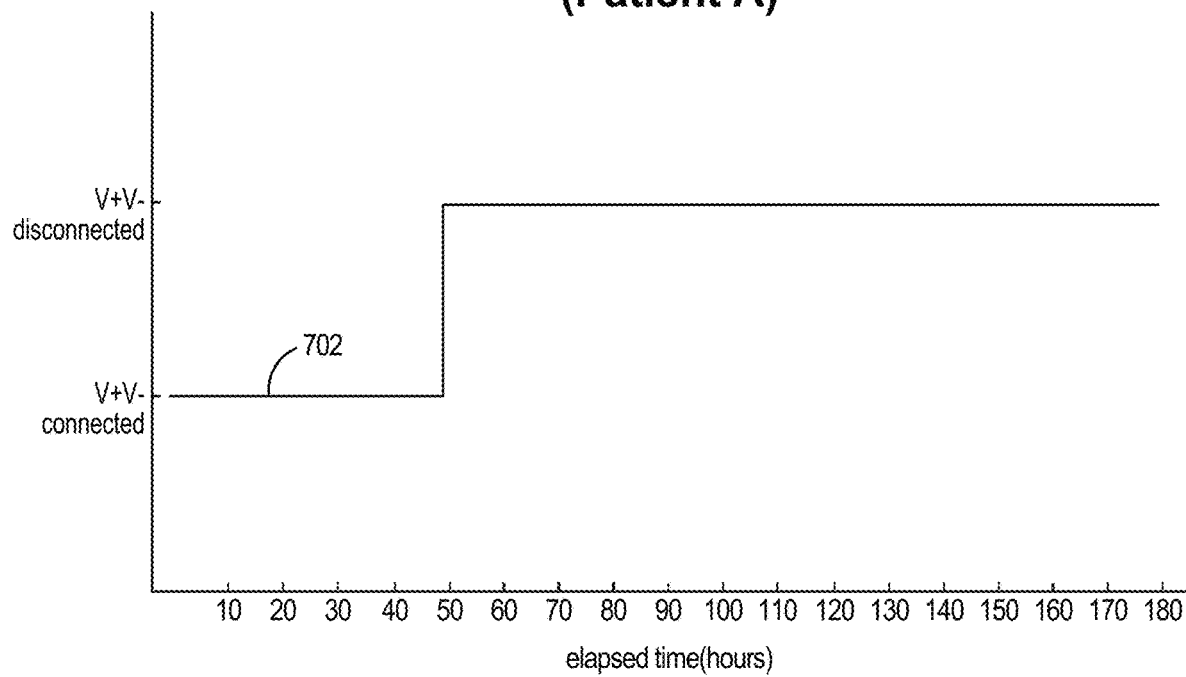

With respect to the example shown in FIG. 7b, the V+/V− integrity flag is persistently onset starting at approximately 50 hours and remains onset for the remainder of the monitoring period. Persistent onset of the V+/V− integrity flag indicates detachment of the device from the patient (i.e., persistent noise). As discussed above, in response to a persistent noise condition an alert may be generated, indicating to one or more of the patient P, the physician, the technician, and/or the remote monitoring center 106 that the signal quality is persistently noisy. In some embodiments, in response to a detected persistent noise state, actions are taken to ensure the patient is wearing the patient medical device and/or to prompt the user to replace the disposable portion with a new disposable portion. In addition, data collection and/or analysis may be halted in response to a persistent noise state.

Figure 7C:
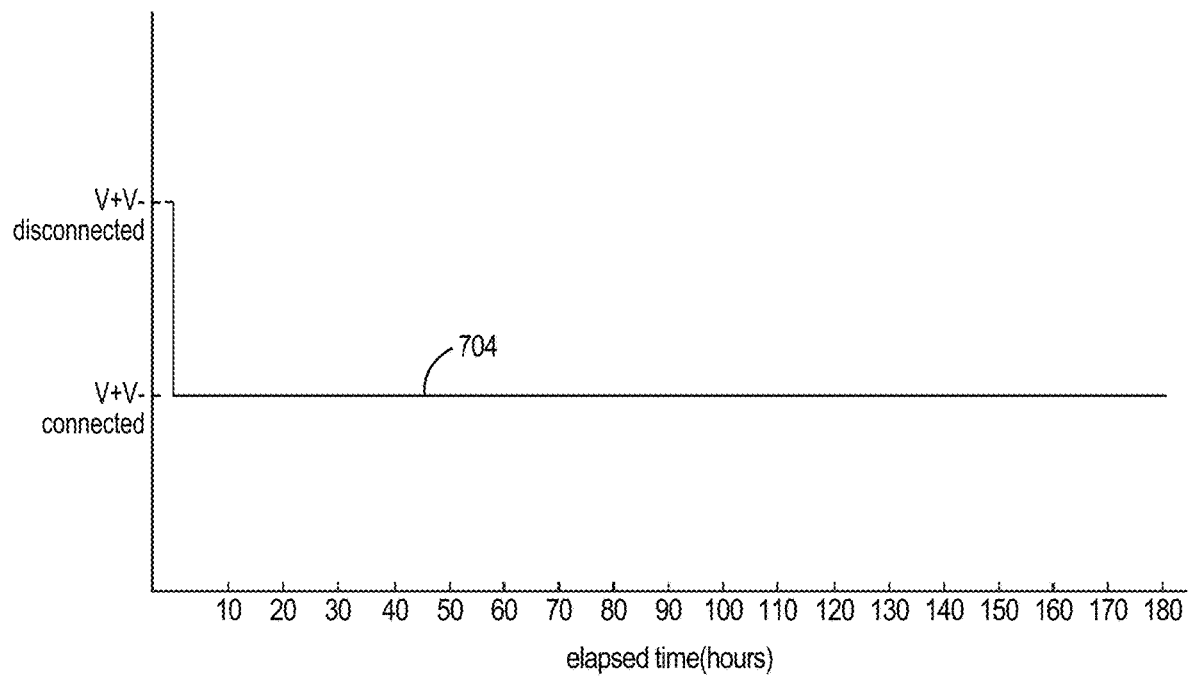

With respect to the example shown in FIG. 7c, the V+/V− integrity flag is onset at the beginning of the monitoring period immediately following attachment of the device to the patient. After a settling period, the V+/V− integrity flag is offset, indicating that the electrical connection is good. In some embodiments, a settling time is required following attachment of the device to the patient, as indicated by the onset of the V+/V− integrity flag at the beginning of the monitoring period. In some embodiments, this is a result of the time required for the hydrogel responsible for ensuring electrical contact between the electrodes and the patient tissue (e.g., skin) is set. In some embodiments, the V+/V− integrity check is utilized at start-up to ensure the patient monitoring device is operating properly.

Figure 7D:
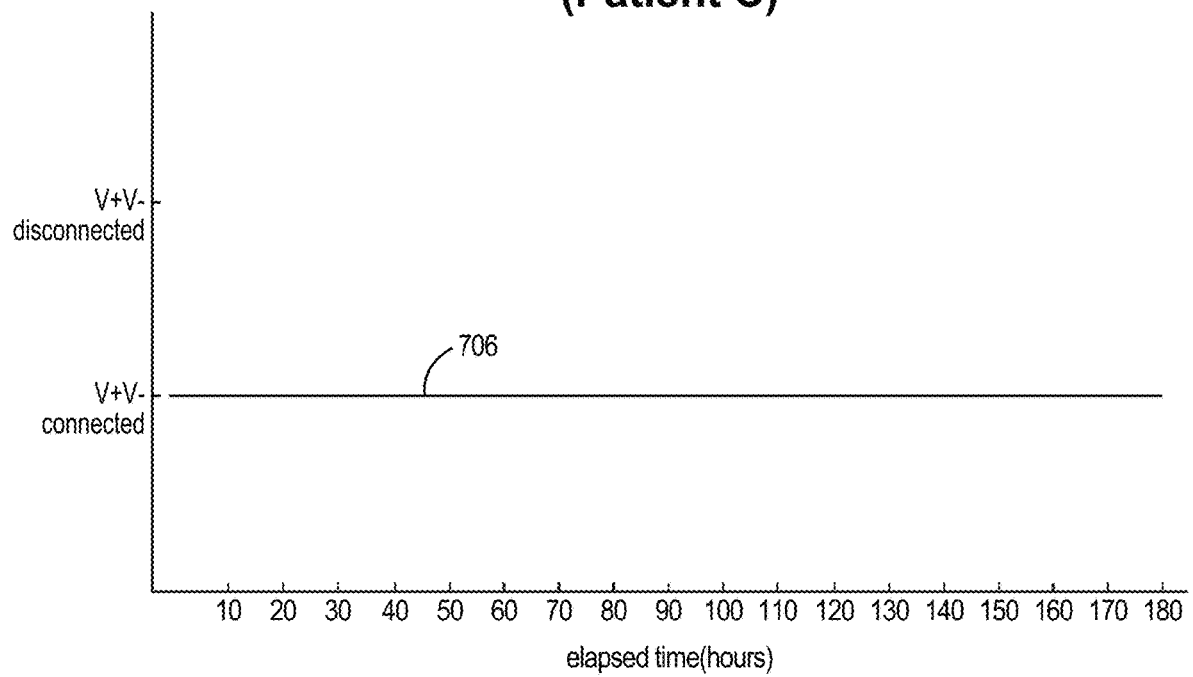

With respect to the example shown in FIG. 7d, the V+/V− integrity flag is not asserted during the monitoring period. In this example, the hydro-gel settling time is very short following attachment of the device to the patient, such that the V+/V− integrity flag is never set. No noise condition— intermittent or persistent—is detected, and no decision is required regarding whether noise is attributable to a settling period or to a noise condition.

FIGS. 8a-8d illustrates embodiments in which the device detach flag is monitored to detect signal quality. In some embodiments, the monitoring device includes at least four electrodes (e.g., electrodes 212a, 212b, 212c, and 212d shown in FIG. 2), any two of which may be referred to as the V+/V− electrodes, and two more which may be referred to as the I+/I− electrodes. In this embodiment, the I+/I− electrodes are utilized by the monitoring device to inject current into the surrounding tissue in order to measure bioimpedance of the surrounding tissue. If the device is detached from the body, the integrity of the I+ to reference can be compromised. In some embodiments, bioimpedance measurements are taken at intervals (e.g., 15 minutes), at which point the integrity of the I+ electrode is determined. Because measurements are not continuous, in some embodiments if the integrity of the I+ electrode indicates a detachment, rather than waiting for the next interval to determine whether the integrity of the I+ electrode has changed, a subsequent measurement is taken at a shorter interval (e.g., 1 minute). In some embodiments, rather than a single measurement following an indication of detachment, a series of measurements are taken at shorter intervals to determine the integrity of the I+ electrode. If each of the measurements indicate that the integrity of the I+ electrode is poor, then a device detach flag is set. As an indication that the device is not attached to the patient or is otherwise noisy, the device detach flag is utilized in some embodiments to confirm a persistent noise state.

Figure 8A:
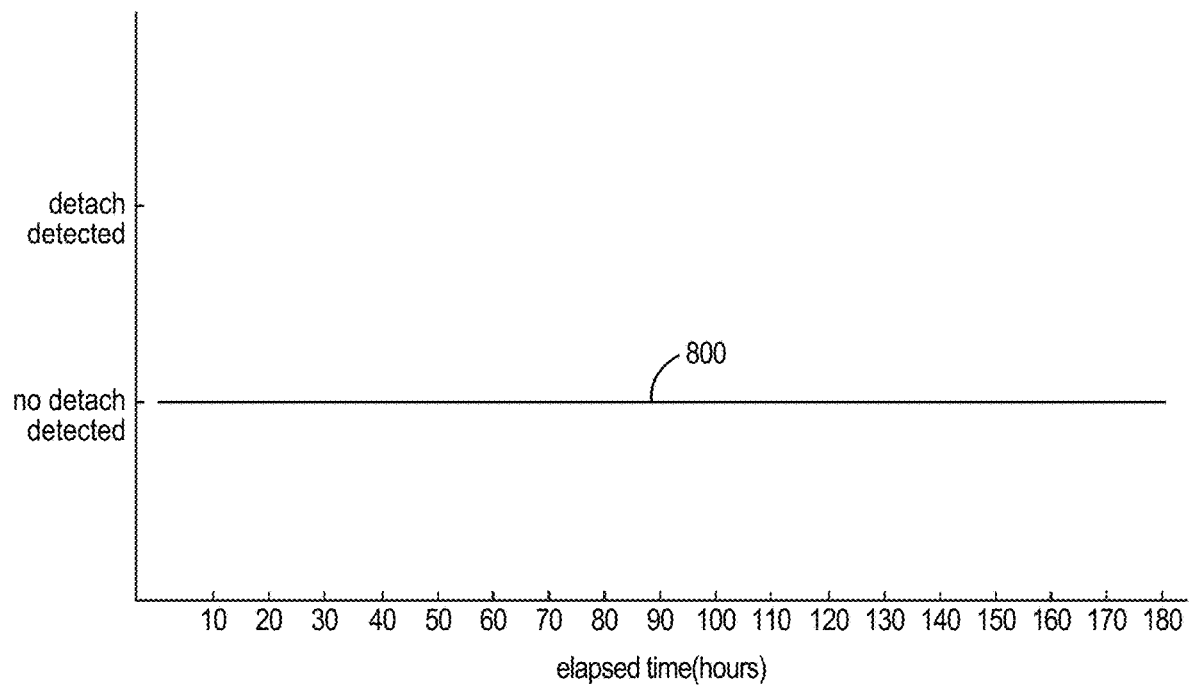
FIGS. 8a-8d are graphs illustrating how the device detach flag is utilized to determine signal quality according to some embodiments.
Figure 8B:
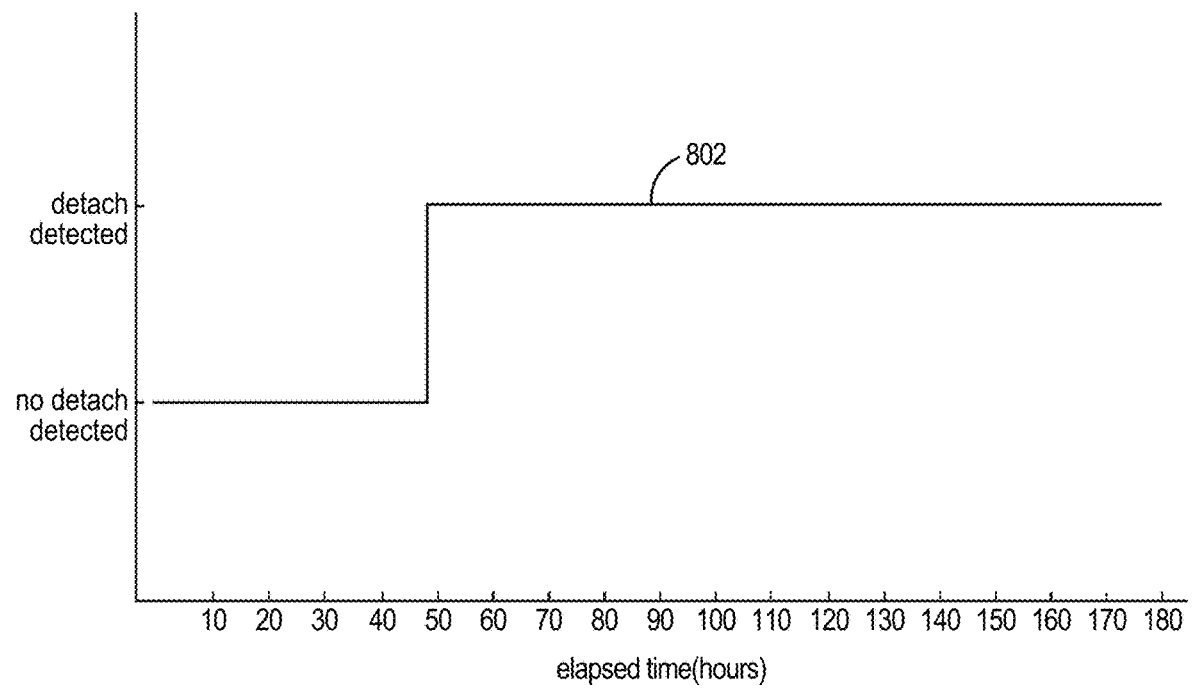
Figure 8C:
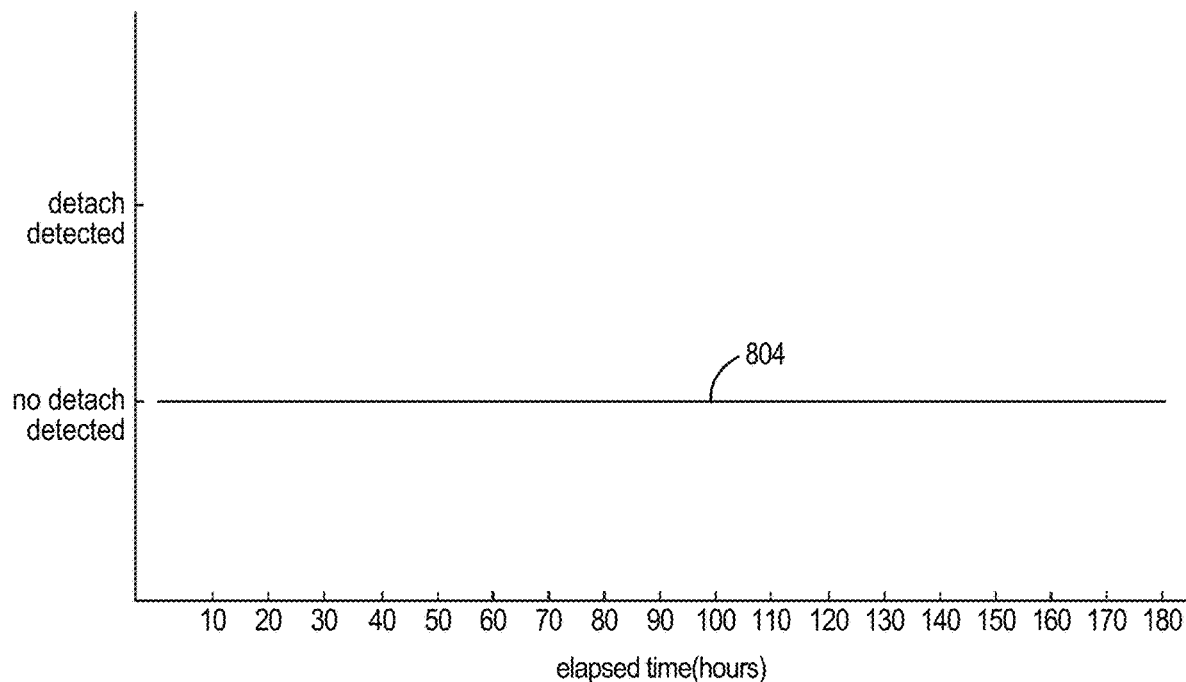
Figure 8D:
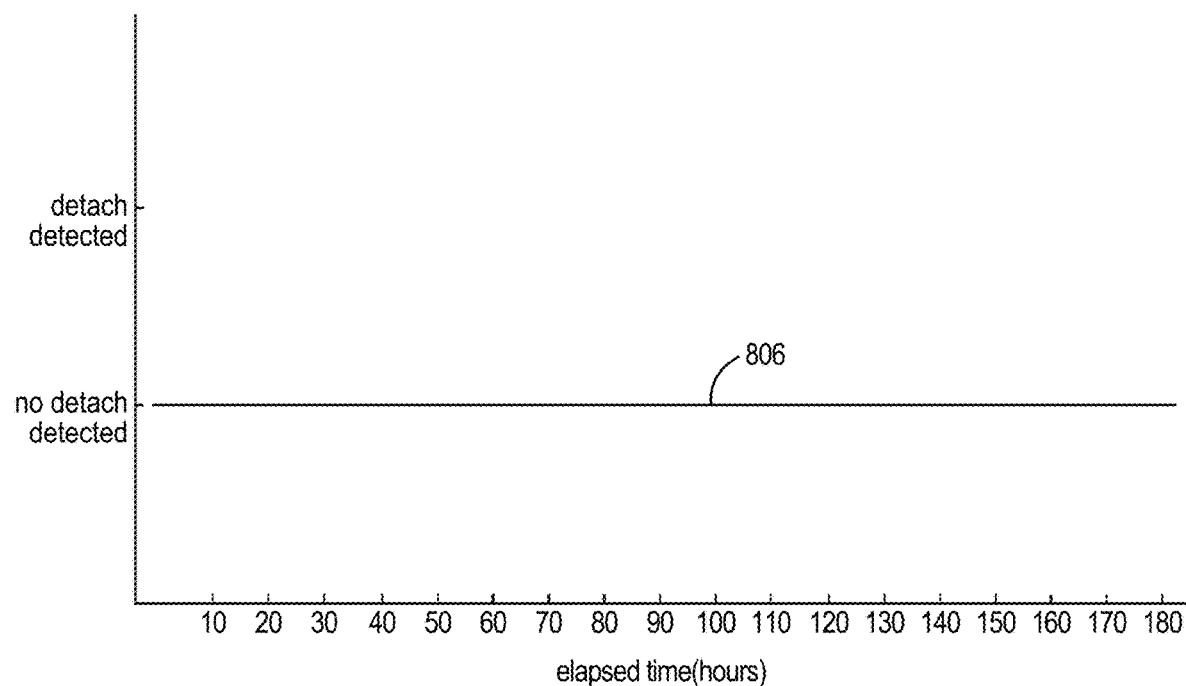

With respect to the monitoring of Patient A shown in FIG. 8a, the device detach flag (line 800) is never onset, indicating that the device is remained attached to the patient throughout the duration of the monitoring period. This does not imply that the signal is not noisy, but is merely one factor in determining signal quality, and in particular in detecting persistent noise conditions. In contrast, with respect to the monitoring of Patient B shown in FIG. 8b, the device detach flag (line 802) is onset at approximately 50 hours and remains onset for the duration of the monitoring period, indicating that the device is not attached or otherwise affixed to the patient during this period (i.e., persistent noise). In response, one or more steps may be taken to address the persistent noise state (e.g., notify one or more of the patient, physician, technician, remote monitoring center 106). With respect to the monitoring of Patients C and D shown in FIGS. 8c and 8d, the device detach flag (lines 804 and 806, respectively) remains offset throughout the duration of the monitoring period, indicating that the patent monitoring device was not persistently removed from the patient. Again, this does not imply that the signal is not noisy, merely that the device is likely attached to the patient.

Differences between V+/V− integrity shown in FIGS. 7a-7d and I+ integrity shown in FIGS. 8a-8d with respect to the same patients is attributable to the frequency at which the integrity checks are completed. For example, V+/V− is monitored at a higher rate than I+ integrity associated with the device detach flag. Hence, settling times associated with first associating the patient monitoring device with a patient were detected by the V+/V− integrity checks, but not with respect to the device detach flag. In this way, the V+/V− integrity flags are a signal quality metric that can be utilized to detect and distinguish between both intermittent and persistent signal quality issues. In contrast, the device detach flag is utilized to detect persistent signal quality issues.

Figure 9A:
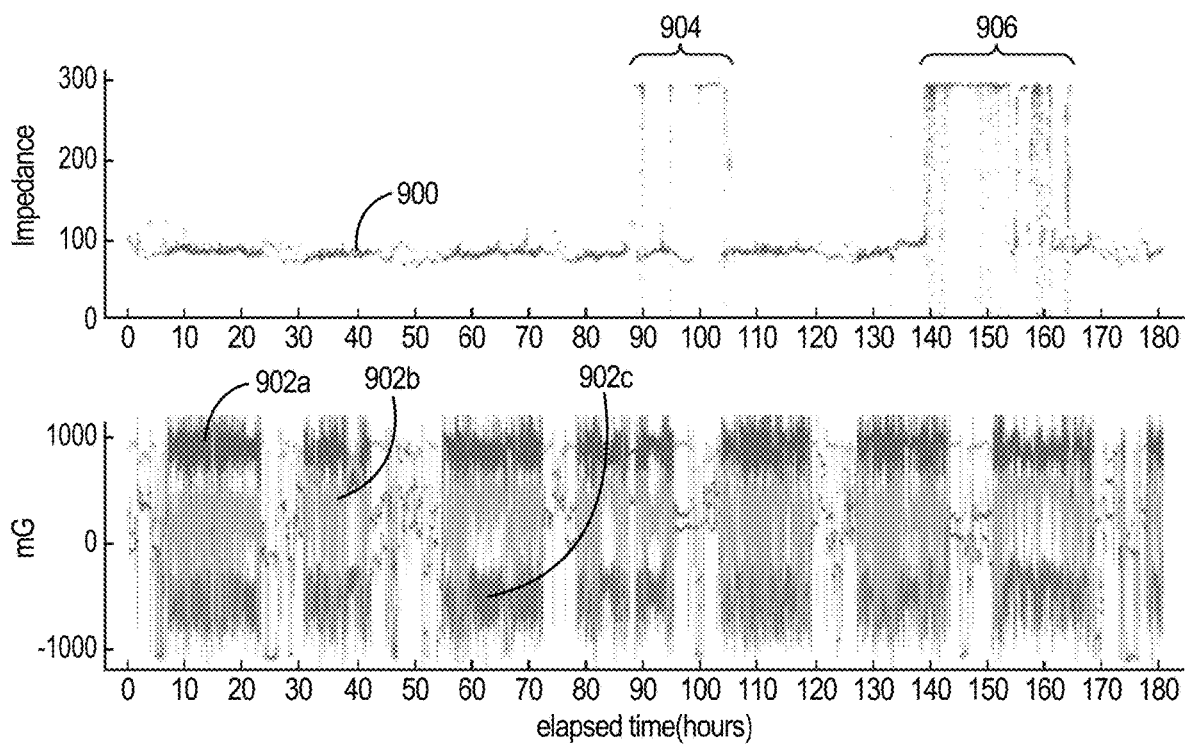
FIGS. 9a-9c are graphs illustrating how bioimpedance and accelerometer measurements are utilized to determine signal quality according to some embodiments.
Figure 9B:
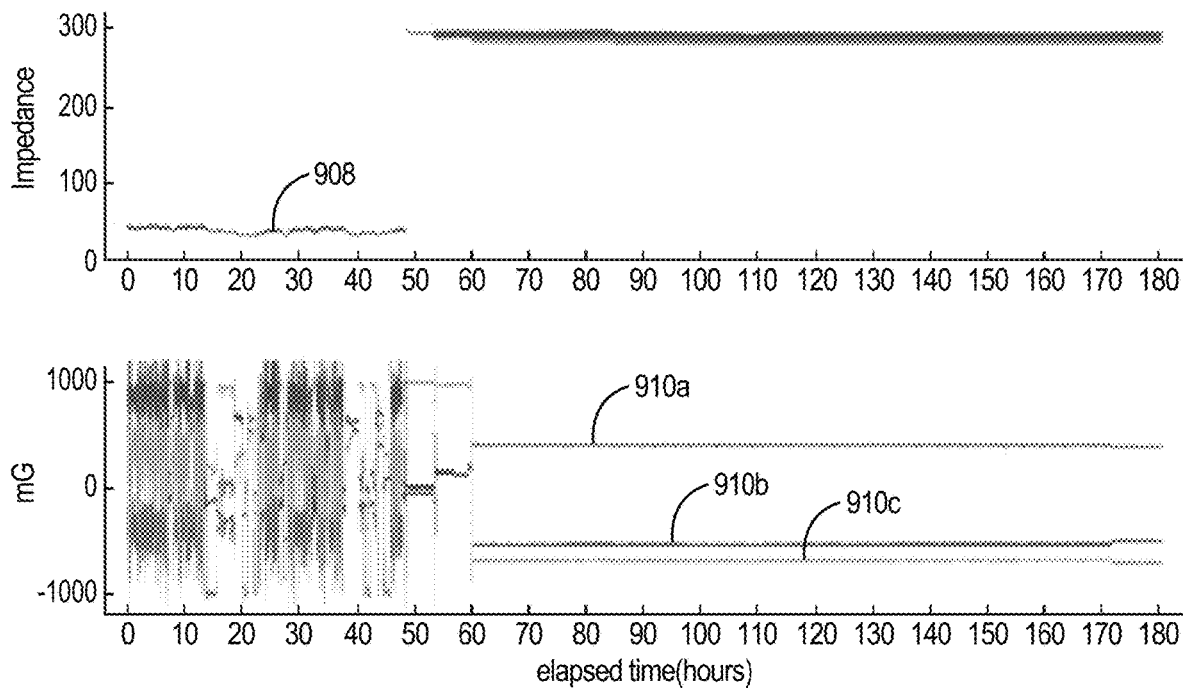
Figure 9C:
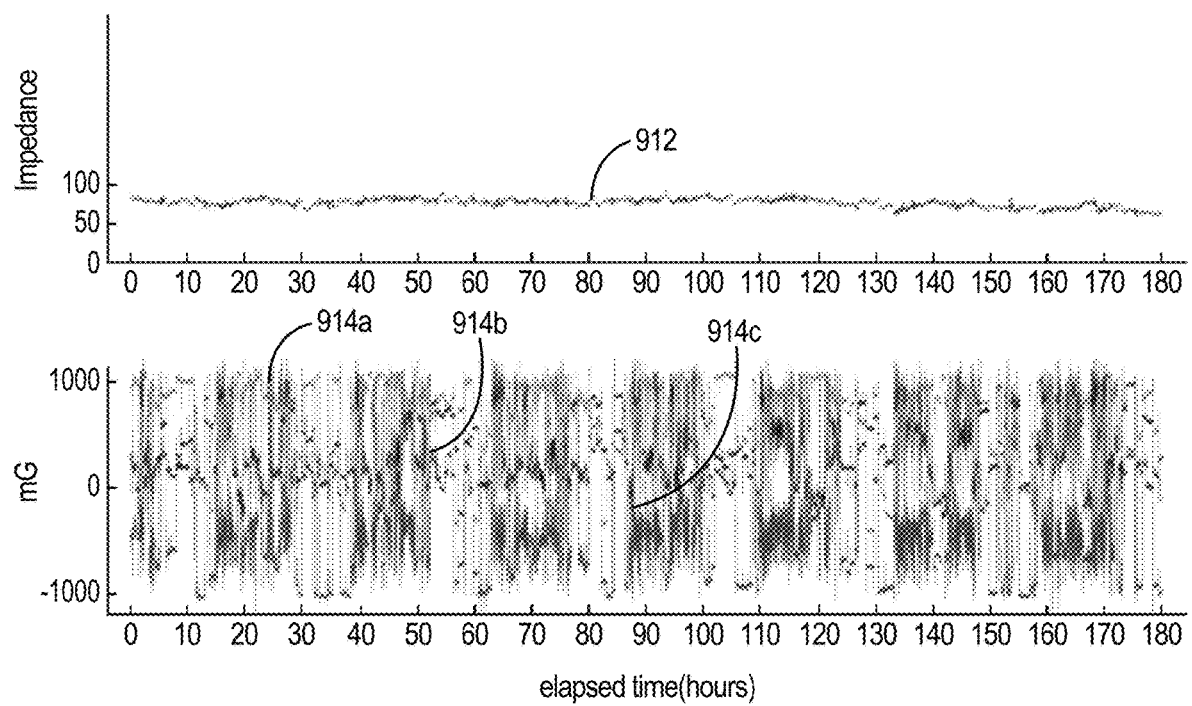

FIGS. 9a-9c illustrate utilization of bioimpedance and accelerometer measurements to determine signal quality. For example, as discussed above, bioimpedance measurements may be taken at regular intervals (e.g., every 15 minutes). Accelerometer measurements may include high-frequency components to detect movement and/or low-frequency components to detect body posture. In some embodiments, a combination of bioimpedance measurements and accelerometer measurements are utilized to make determinations regarding signal quality. For example, abnormal variation in monitored bioimpedance values coupled with normal variation in accelerometer measurements indicates partial device attachment and intermittent noise in monitored signals. With respect to Patient A shown in FIG. 9a, the top graph illustrates measured bioimpedance (line 900) while the bottom graph illustrates accelerometer measurements taken along the x, y, and z axis as shown by lines 902a, 902b, and 902c. As shown in this example, the measured impedance illustrates abnormal variation at period 904 and 906, while the measured accelerometer signals indicate normal variation throughout the monitoring period. The combination of normal variation in the measured accelerometer and abnormal variation in the bioimpedance measurements indicates partial detachment of the monitoring device (i.e., still affixed to the body, as indicated by normal variation in accelerometer measurements). As a result, the error state may be identified as intermittent.

With respect to Patient B shown in FIG. 9b, the bioimpedance signal (shown in the top graph, line 908) shows normal variation initially, but then becomes abnormally high starting at approximately 50 hours and remaining so for the duration of the monitoring period. Similarly, the accelerometer measurements (lines 910a, 910b, and 910c) illustrate normal variation initially, but then show abnormally low variation starting at approximately 50 hours. The combination of abnormally high biompedance measurements along with abnormally low variation in the accelerometer measurements at hour 50 indicates that the device has been removed and placed, for example, on a table. This type of noise would be classified as persistent.

With respect to Patient C shown in FIG. 9c, both the bioimpedance signal (shown in the top graph, line 912) and the accelerometer measurements shown normal variation throughout the monitoring period (lines 914a, 914b, and 914c). This indicates persistent wear of the patient monitoring device throughout the monitoring period and indicates normal ECG and bioimpedance signal quality.

In some embodiments, the measure of variability is based on a determination of the standard deviation measured with a moving window (e.g., 4-hour moving window). In some embodiments, the measure of variability in the accelerometer measurements is measured as the total power in the higher frequencies and the number of DC-shifts in the accelerometer signals within a moving window (e.g., 2-hour moving window). For example, very little high-frequency power and/or few DC shifts indicate low accelerometer variation. These measurements may be compared to threshold values to determine whether the measured signals indicate high or low levels of variability.

Figure 10A:
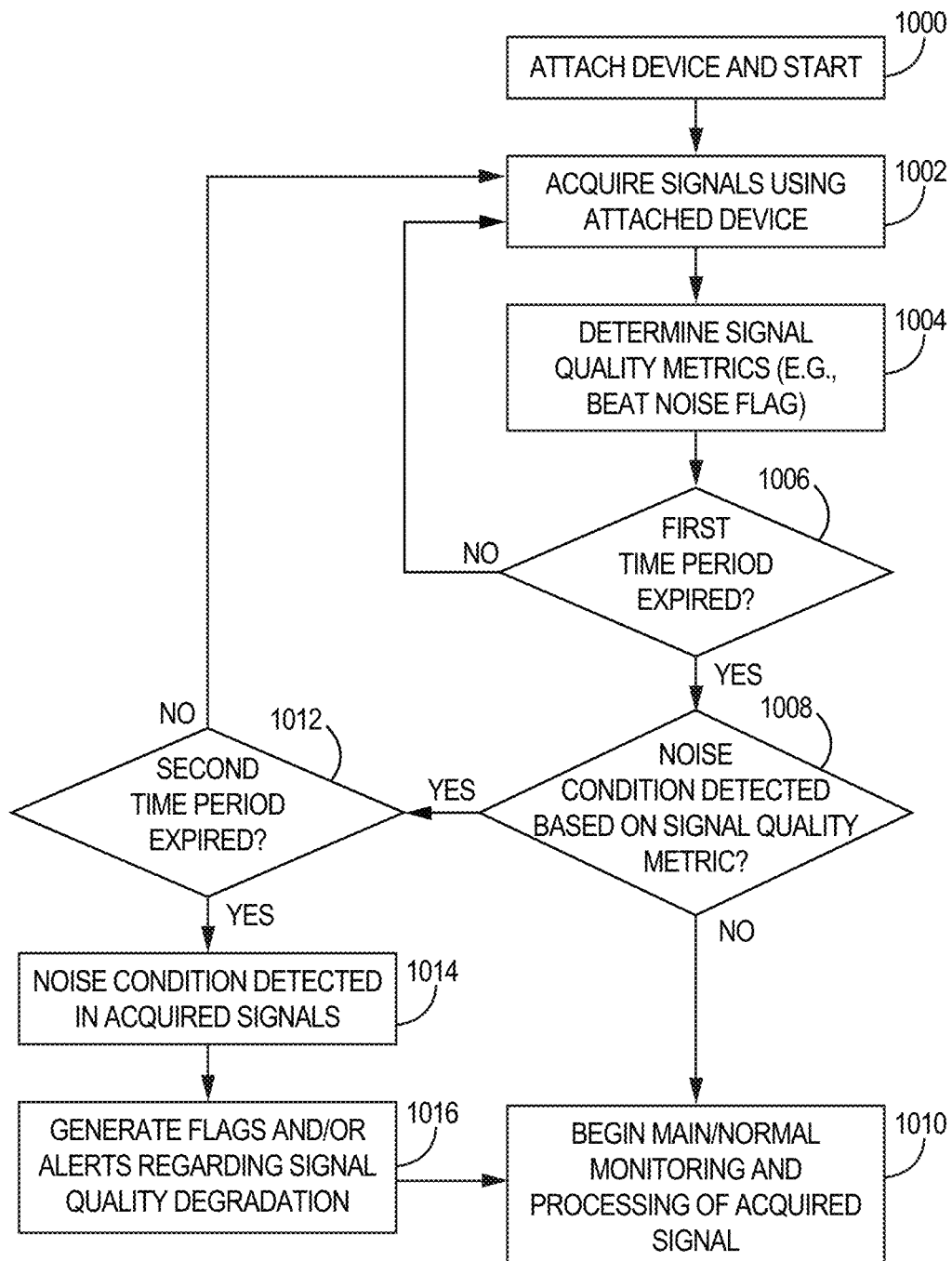
FIGS. 10a and 10b are flowcharts that illustrate methods of determining signal quality at initialization according to some embodiments.
Figure 10B:
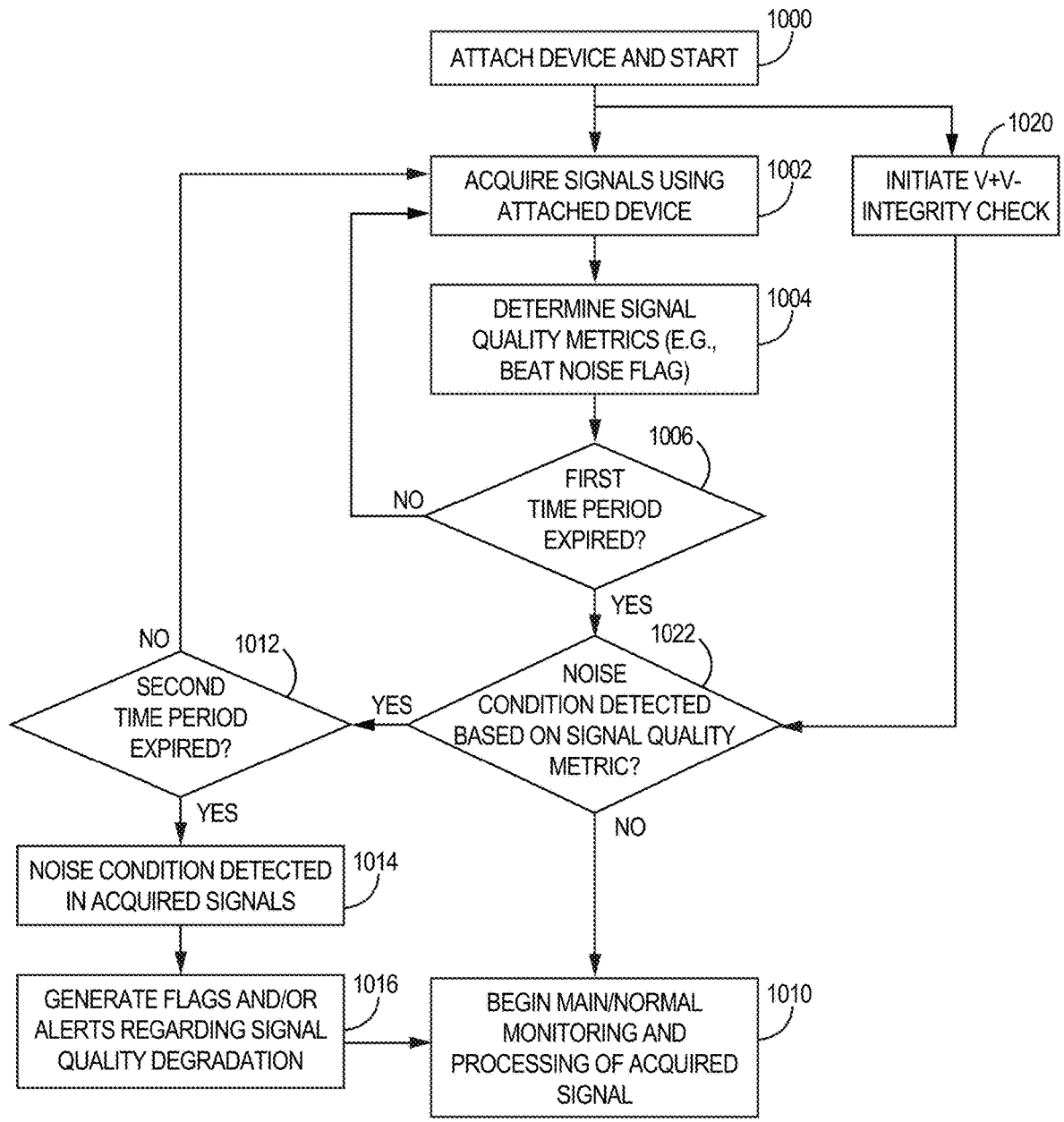

FIGS. 10*a* and 10*b* are flowcharts that illustrates a method of determining signal quality at initialization according to some embodiments. In some embodiments, patient monitoring devices are turned On automatically upon being applied to the patient. For example, adherent devices may be configured to turn On automatically when applied to the skin of a patient. In these applications, the time required for the monitored signals to "settle" may differ depending on a number of factors, including readjustment of the device by the patient and/or physician. During this time, measurements may be affected by noise. FIGS. 10*a* and 10*b* illustrate methods of monitoring the settle time at startup to determine when normal monitoring may begin. In the embodiment shown in FIG. 10*a*, beat noise flags are utilized to determine when signal quality is sufficient to being monitoring and/or analyzing monitored data. In the embodiment shown in FIG. 10*b*, beat noise flags are utilized in combination with V+/V− integrity checks to determine when signal quality is sufficient to being monitoring and/or analyzing monitored data.

With respect to FIG. 10*a*, the method starts at step 1000, the patient monitoring device is attached or otherwise affixed to the patient and monitoring begins. As discussed above, monitoring may be initiated either automatically or be initiated manually. At step 1002, signals are acquired from the patient monitoring device. At steps 1004 and 1006, signal quality metrics are determined from the one or more signals acquired at step 10002, and continues for a first duration of time (e.g., until the elapsed time exceeds the first threshold). For example, in some embodiments, the signal quality metric is a beat noise flag determination based on an analysis of the monitored ECG signal for the presence of high-frequency noise (e.g., muscle-induced artifacts), ECG signal clipping noise, electrode motion noise, low-amplitude QRS noise, and/or spike noise. If any of these noise elements are detected, the beat is noisy and is identified with a beat noise flag. In some embodiments, signals acquired during the first duration of time are stored but not analyzed for beat detection noise flagging until the first duration of time has ended. In other embodiments, the monitored signals are analyzed in real-time or near real-time for beat detection noise flagging. In some embodiments, the first duration of time (i.e., first time period) must expire prior to determining signal quality metrics, wherein the first duration of time is selected to accommodate a settling time associated with the patient monitoring device (i.e., performing the determination at step 1006 prior to the determination at step 1004). In some embodiments the first duration of time is predetermined based on the type of device (e.g., 5 minutes, 15 minutes, etc.). In other embodiments, the first duration of time is determined based on one or more other factors. For example, in one embodiment the first duration of time requires that activity level be low and therefore may be paused in the event excessive patient movement is detected.

At step 1008, a noise condition determination is made based on the signal quality metrics acquired during the first time period. For example, in embodiments in which beat noise flags are utilized as the signal quality metric, the number of beat noise flags detected within the first time period is compared to a threshold value. For example, in one embodiment the determination may review whether a number X of the last Y beats were flagged as noisy (e.g., 20 of the last 25 beats flagged as noisy). If the determination at step 1008 indicates that the signal is not noisy (i.e., fewer than X of the last Y beats are noisy), the normal monitoring and processing of the acquired signal begins at step 1010. In some embodiments, normal monitoring and processing of acquired signals includes capturing baseline data such as baseline patient ECG morphology, baseline heart rate (HR) information, etc. This may also include capturing baseline data associated with other physiological parameters. Following capture of baseline data, normal monitoring and processing of acquired signal may include applying automatic arrhythmia detection algorithms and other physiological monitoring algorithms. With respect to patient monitoring devices—such as Holter monitors—a determination that the signal quality is not noisy at step 1008 is utilized as the start time for monitoring and recording ECG data for subsequent analysis.

If the determination at step 1008 indicates the presence of an abnormally large number of noisy beats (i.e., X of the last Y beats are flagged as noisy), then a determination is made that the settling time is ongoing as evidence by the detected poor signal quality. As described above, a settling time is required at initialization that varies from patient to patient based on a number of factors. In response to a determination that the signal quality is noisy, then the process continues monitoring for an additional period of time determined by the second threshold at step 1012. During this time, additional ECG signal are acquired at step 1002 and beats are analyzed as described above to detect beat noise flags. If at any point during this time the determination at step 1008 indicates a good, non-noisy signal (e.g., fewer than X of the last Y beats are noisy), then at step 1010 normal monitoring and processing of the acquired signals begins. However, in the event the elapsed time from the start of monitoring exceeds the second threshold prior to a determination that the signal is non-noisy (as determined at step 1012), then a determination is made at step 1014 that the quality of the signal is noisy. In some embodiments, at step 1016 a notification is generated alerting one or more of the patient P, health care professional, the physician, the technician, and/or the remote monitoring center 106 of the noisy signal quality. For example, with respect to the adherent device shown in FIG. 3, the alert may result in triggering of first alert 302, indicating to the patient that the patient monitoring device needs to be re-positioned. In some embodiments, if the patient and/or technician modifies the position of the patient monitoring device, the initialization process is restarted in order to allow the patient monitoring device time to settle prior to recording and/or processing data.

In some embodiments, despite a determination at steps 1014 and 1016 that the signal quality is noisy, monitoring and/or processing of the acquired signals begins at step 1010. In some embodiments, a determination of poor signal quality is utilized during processing of acquired signals. For example, a weighting factor or significance may be assigned to the acquired signals indicating that the reliability of diagnosis (e.g., detected arrhythmias, etc.) based on the signals is lower than usual. In addition, in some embodiments monitoring of the ECG signal continues and signal quality is re-assessed at a later point in time, wherein the re-assessment may utilize the same steps provided in FIG. 10*a* to determine the status of the signal quality based on the measured beat noise flags.

In this way, signal quality of a patient monitoring device is determined based on analysis of ECG data collected by the patient monitoring device. In the embodiment shown in FIG. 10*a*, the determination of signal quality is made based only on the ECG signal-based measure of beat noise flags. In other embodiments, additional ECG signal-based measures may be utilized, as well as one or more measured on the electrical design of the patient monitoring device or one or more other sensors. For example, FIG. 10*b* illustrates an embodiment in which in addition to the beat noise flag metric (or other ECG based metrics), one or more measurements based on electrical design of the patient monitoring device is utilized to determine initial signal quality. In the embodiment shown in FIG. 10b, while ECG signals are being acquired and analyzed to determine beat noise flags, a V+/V− integrity check is initiated at step 1020. As described above, the V+/V− integrity check monitors the voltage between two of the ECG electrodes (labeled here as "V+" and "V−").

At step 1022, the V+/V− integrity check is utilized in combination with the ECG based quality measures (e.g., beat noise flags) to determine signal quality. In one embodiment, if either the V+/V− integrity flag is set (indicating a disconnect between the electrodes) or at least X of the last Y beats are noisy, then the signal is determined to be of low quality. In other embodiments, both the V+/V− integrity flag and at least X of the last Y beats are determined to be noisy are required to make a determination that the signal quality is low. In this way, a combination of ECG based signal measures and signals based on the electrical design of the patient monitoring device are utilized to determine signal quality prior to initiating the main/normal monitoring and processing of acquired signals.

FIGS. 10a and 10b provide a method of determining at startup whether signal quality of the device. The method takes into account the settling time required for devices when first adhered/affixed to a patient, and utilizes attributes of signals monitored by the device (e.g., noise beat flags associated with ECG signals) to make a determination regarding signal quality. In particular, this is not merely a check of whether the device is electrically and/or mechanically adhered to the patient, but rather an assessment of signal quality at initialization that ensures the data collected during the monitoring period will have diagnostic value.

Figure 11:
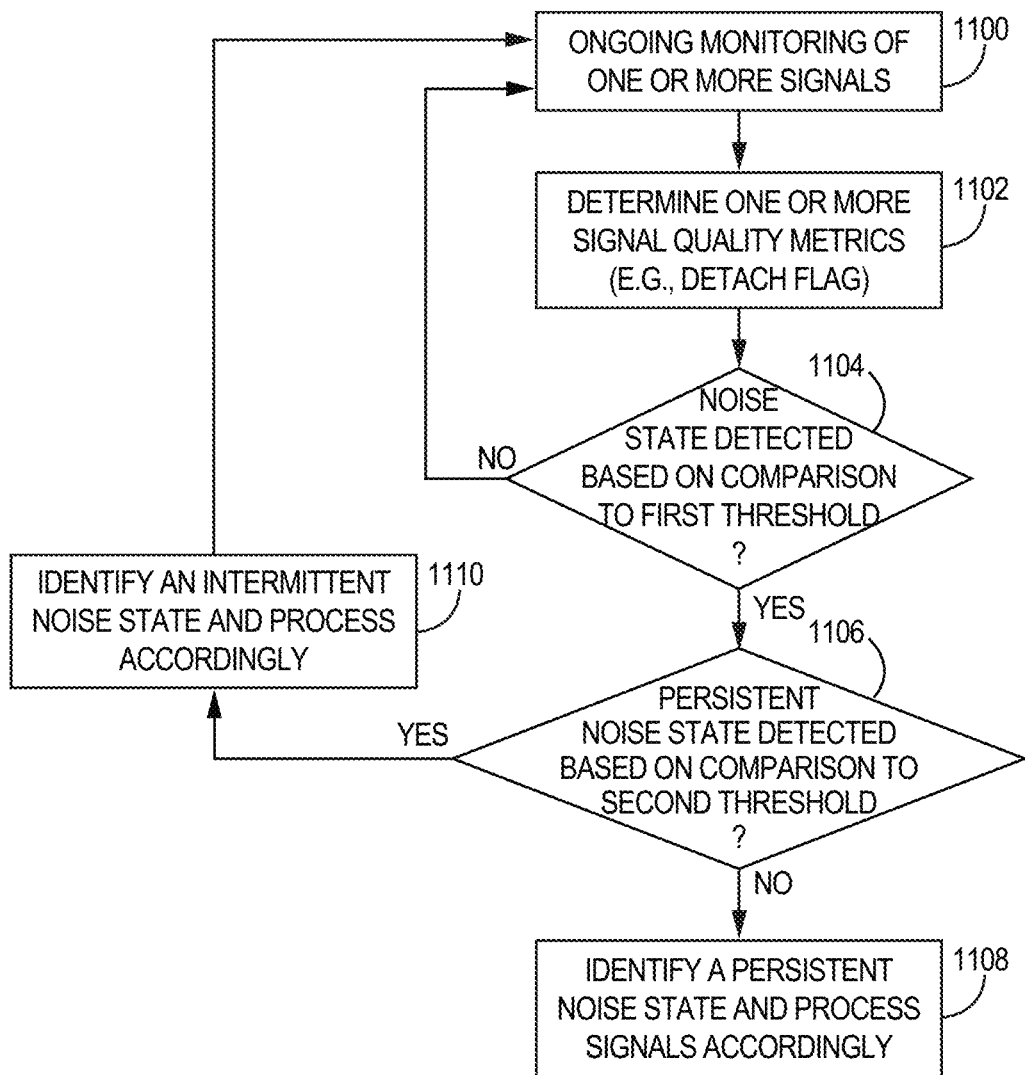
FIG. 11 is a flowchart that illustrates a method of monitoring signal quality in which two or more sensitivity/specificity levels are utilized to detect and differentiate between intermittent noise and persistent noise according to some embodiments.
Figure 12:
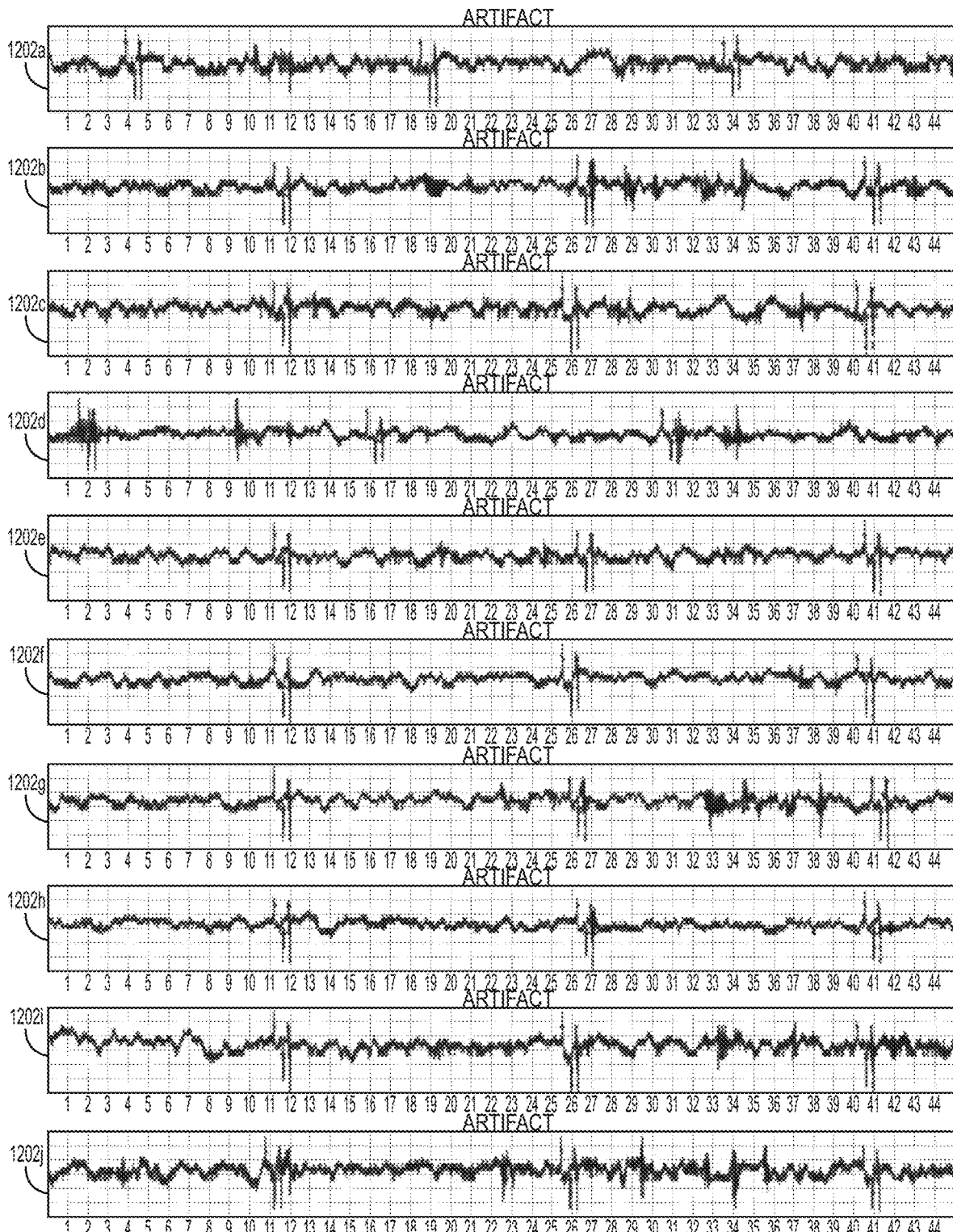
FIG. 12 illustrates the display of a plurality of signals identified as noisy in a way that reduces the amount of time a technician/reviewer must spend reviewing the data signals according to some embodiments.
Figure 13:
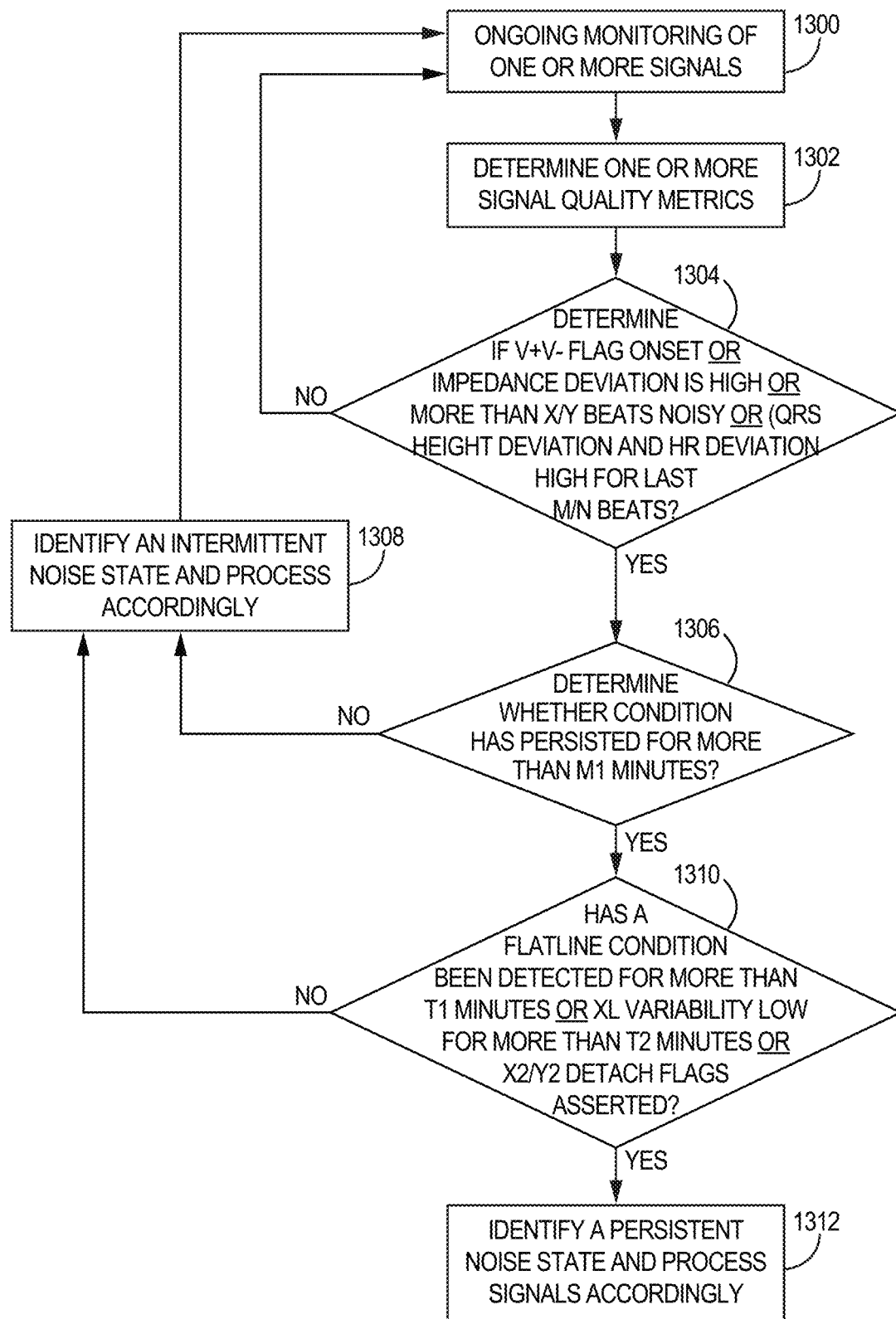
FIG. 13 is a flowchart that illustrates a method in which a combination of different signal quality metrics are combined to form a multi-parameter indicator of signal quality according to some embodiments.

FIGS. 11-13 are flowcharts illustrating various methods of monitoring signal quality during the monitoring period. In general, the methods described with respect to FIG. 11-13 detect and distinguish between intermittent signal quality noise and persistent signal quality noise. The remedy for intermittent signal quality deterioration may be to flag those segments affected to prevent analysis of those segments, weight the results of those segments appropriately, and/or apply additional signal processing to those segments. In contrast, the remedy for persistent signal quality deterioration may be to initiate a replacement/repositioning of the patient monitoring device, identify non-compliance by the patient in removing the patient monitoring device before the end of the monitoring period, and/or monitor workflow management in the remote monitoring center by either discarding those segments associated with persistent signal quality deterioration or grouping them in a way that makes it easy for a technician to review and dismiss large amounts of signal data related to persistent signal quality deterioration.

In particular. FIG. 11 illustrates a method of monitoring signal quality in which two or more sensitivity/specificity levels are utilized to detect and differentiate between intermittent noise and persistent noise.

At step 1100, one or more signals are measured in ongoing fashion. This may include ECG based signals as well as signals based on electrical design and/or other sensors. At step 1102, one or more signal quality metrics are detected, and may include ECG signal-based measures such as beat noise flags. ECG flatline detection, deviation in QRS height and detected heart rate, as well as one or more measures based on electrical design, including V+/V− integrity checks, device detach flags, and/or bioimpedance/accelerometer measurements. For example, in the embodiment shown in FIG. 11, the device detach flag is utilized to detect and distinguish between intermittent and persistent signal quality issues.

At step 1104, an initial signal quality determination is made based on one or more of the signal quality metrics. If the initial signal quality determination does not indicate a signal quality issue, then ongoing measurements of the one or more signals continues at step 1100. If the initial signal quality determination does indicate a signal quality issue, then at step 1106 a secondary signal quality determination is made based on one or more of the signal quality metrics. In the embodiment shown in FIG. 11, the same signal quality metric utilized at step 1104 is utilized at step 1106, albeit with a different sensitivity level. At step 1104, the signal quality metric is compared to a sensitive threshold (e.g., more sensitive than the threshold utilized at step 1106) in order to detect both intermittent and persistent signal quality issues. For example, in one embodiment the signal quality metric relied on is the detach flag, described above, in which the integrity of the electrode (e.g., I+) utilized to inject current into the surrounding tissue as part of a bioimpedance measurement is monitored. If the integrity of the electrode as compared with a reference indicates that the electrode is not attached to the patient, then the device detach flag is set. At step 1104, if a number X1 of the last Y1 device detach flags is set, this indicates the presence of noise (either intermittent or persistent). For example, in one embodiment if one of the last ten device detach flags is set, then noise is detected at step 1104.

At step 1106, a second threshold is applied to the signal quality metric to distinguish between intermittent noise conditions and persistent noise conditions. As compared to the first threshold, the second threshold is less sensitive but more specific. For example, in one embodiment the second threshold is met if each of the last X2 device detach flags were asserted or set (i.e., seven of the last seven device detach flags). As compared to the first threshold, the second threshold is utilized to distinguish between intermittent noise and persistent noise. If the second threshold is not met, then at step 1110 an intermittent noise state is detected and one or more actions are taken based on the type of monitoring being performed. In the embodiment shown in FIG. 11, the same signal metric (e.g., device detach flag) utilized at step 1104 is utilized at step 1106. However, in other embodiments a different signal quality metric is utilized.

For example, in some embodiments the identification of intermittent noise may be associated with signals captured during the noise period. This may include data segments identified as indicative of an underlying condition (e.g., arrhythmia). In some embodiments, the review of data segments flagged as including intermittent noise are deprioritized. These data segments (e.g., ECG segments) may still be recorded and/or communicated to a remote monitoring center for review, but may be placed into a different (e.g., lower priority queue) for review. In some embodiments, data segments that are deprioritized or included in the lower priority queue are presented for review in a way that allows the reviewer to quickly assess whether any of the data requires further review. An example is shown in FIG. 12, in which a plurality of data segments 1202a-1202j flagged as including intermittent noise are displayed at one time for an HCP or technician to review. Those segments determined by the technician to include useful data may be selected and moved to a higher priority queue for more detailed review. The remaining data segments may then be discarded. In other embodiments, a plurality of data segments may be flagged indicating a persistent noise state, with the plurality of segments being displayed at one time for a technician or HCP to quickly review to confirm the persistent noise state detected.

With respect to Holter-type monitoring, in which monitored signal data is stored locally but not analyzed, a determination of intermittent noise may be handled in a number of ways. In one embodiment, all date (e.g., ECG data) is presented for review but markers are included in the data indicating segments associated with intermittent noise that may be skipped or given less weight by the manual review technician. In other embodiments, the intermittently noisy segments are automatically removed (but not deleted) from the data collected and the remaining data (e.g., non-noisy ECG segments) are stitched together to provide a clean signal for manual review by a technician. If necessary, the noisy segments may be reviewed by the technician if necessary and/or desirable. In other embodiments, the data collected by the Holter-type monitor is broken up into a plurality of smaller segments and only the non-noisy segments are retained for subsequent review. In this way, only non-noisy segments are recorded for subsequent manual review by a technician, decreasing the total amount of data that must be reviewed at the risk of losing data that may be potentially relevant.

In addition to the steps described above for handling intermittently noisy data, steps may also be taken to alert one or more of the patient P, physician, technician, and/or remote monitoring center 106 regarding the detected intermittent noise. For example, in one embodiment, first alert 302 (shown in FIG. 3) is activated to alert the patient to the intermittent noise condition. In response, the patient P may alter behavior (e.g., stop an activity, change activities, etc.) to improve the signal quality, reposition the device, etc.

If the second threshold is met, then at step 1108 a persistent noise state is detected and one or more actions are taken. In some embodiments, this may include discontinuing the monitoring/storing of data signals. For example, a Holter monitor utilizing to record signals may discontinue the recording of data signals in response to a detected persistent noise state. In other embodiments, data signals that are collected subsequent to a detected persistent noise state may be identified as such. In some embodiments, data signals flagged as corresponding to a persistent noise state are not processed/analyzed either locally or at the remote monitoring center. For example, in response to persistent noise some patient monitoring devices may cease monitoring and/or recording data signals. In some embodiments, data signals flagged as corresponding to a persistent noise state are not communicated to the remote monitoring center. In some embodiments, data signals flagged as corresponding to a persistent noise state are identified as such as subsequent processing of the data signals takes into account the persistent noise state. For example, in some embodiments, rather than providing each segment of data to a technician for review at the remote monitoring center, each of the segments of data corresponding to a persistent noise state are collected and grouped together and presented to the user to allow for a cursory review of all data related to the persistent noise state. A benefit of this approach is that it does not required the technician to review a plurality of segments individually, rather the technician can review the plurality of segments quickly and determine that the noise state is in fact persistent and does not require additional review.

In addition, in response to a detected persistent noise state, a notification may be provided to one or more of the patient P, the physician, and/or the monitoring center. In some embodiments, a persistent noise state may be utilized as an indication that the patient needs to change the patient monitoring device (e.g., attach a new device). In some embodiments, in response to a persistent noise state, second alert 304 is activated to notify the patient that the life of the patient monitoring device has expired and that a new patient monitoring device should be affixed to the patient. In some embodiments, in response to a detected persistent noise state a notification is provided to the remote monitoring center, which proceeds to check in with the patient P to determine patient status (e.g., patient is wearing the patient monitoring device, it is attached correctly, etc.). In this way, signal quality metrics are utilized to distinguish between different noise states (intermittent, persistent) and take action accordingly.

FIG. 13 illustrates a method in which a combination of different signal quality metrics are combined to form a multi-parameter indicator of ECG signal noise.

At step 1300, one or more signals are measured in ongoing fashion. This may include ECG based signals as well as signals based on electrical design and/or other sensors. At step 1302, one or more signal quality metrics are detected, and may include ECG signal-based quality measures such as beat noise flags. ECG flatline detection, deviation in QRS height and detected heart rate, as well as one or more measures based on electrical design, including V+N-integrity checks, device detach flags, and/or bioimpedance/accelerometer measurements. For example, in the embodiment shown in FIG. 13, one or more of V+/V− integrity check, bioimpedance deviation, beat noise flags, QRS height deviation, and/or HR deviation are utilized.

At step 1304, a combination of signal quality metrics are compared to various thresholds to detect signal quality. For example, in the embodiment shown in FIG. 13, V+/V− integrity check, bioimpedance deviation, beat noise flags. QRS height deviation, and/or HR deviation are utilized. In this embodiment, a signal quality problem is detected if one of the V+/V− integrity check is onset, the bioimpedance deviation is greater than a threshold, beat noise flag is greater than a threshold (e.g., a number X of the last Y beats have been flagged as noisy), or both QRS height deviation and heart rate (HR) deviation has been greater than a threshold for a certain number of beats (e.g., a number M of the last N beats). In this example, a combination of ECG-based signal quality metrics (beat noise flags. QRS height deviation, and HR deviation) are utilized in combination with other signal quality metrics (e.g., V+/V− integrity checks, and bioimpedance deviation) to detect signal quality issues (e.g., noise).

At step 1306, a determination is made regarding how long the condition has persisted. In one embodiment, if the noisy signal quality condition has not persisted for longer than a threshold (e.g., M1 minutes), then at step 1308 the signal quality (for the time being) is identified as intermittently noisy and ongoing measurement continues at step 1300. If at step 1306 it is determined that the noisy signal quality condition has persisted for longer than the threshold (e.g., M1 minutes), then at step 1310 additional signal quality metrics are analyzed to confirm whether the signal quality condition is persistent or intermittent. In some embodiments, the additional signal quality metrics include one or more of flatline detection, accelerometer variability and/or detach flags. In one embodiment, a persistent signal quality noise condition is detected if at least one of signal quality metrics indicates a noise condition. For example, if the flatline metric persists for a period (e.g., T1 minutes), or accelerometer variation is low for a period (e.g., T2 minutes) or detach flags are set then the signal quality issue is identified as persistent. If none of the signal quality metrics at step 1310 indicate a persistent noise condition, then the noise condition is identified as intermittent at step 1308.

A determination at step 1306 or 1310 that the noise condition is intermittent may result in one or more actions being taken, as discussed with respect to other embodiments. These include flagging/notifying downstream algorithms of the intermittent noise condition, allowing the algorithms to appropriately weight and/or de-emphasize the data analyzed, providing notifications to one or more of the patient P, the physician, the technician, or the remote monitoring center regarding the detected intermittent noise condition. Furthermore, continuing monitoring of one or more signal quality metrics and comparison to thresholds at steps 1304, 1306 and 1308 may result in a change in the noise condition status, either as an improvement indicating that the signal is (essentially) noise free or a downgrade in which the signal is determined to be persistently noisy.

At step 1312, a persistent noise condition is identified and steps are taken in response to this determination. As discussed above, identifying a persistent noise condition determines how signal data is captured and/or processed, and may differ from determinations that the noise condition is intermittent. For example, in some embodiments data recording may be halted/suspended in response to a detected persistent noise state. Similarly, flag/notifications may be set alerting downstream processing algorithms of the persistent noise condition, allowing these algorithms to properly weight or de-emphasize data signals flagged as persistently noisy. In addition, alerts may be generated requesting the user to replace the device, or to ensure that the patient is utilizing/wearing the patient monitoring device. As discussed above, persistent noise in adherent device is often-times an indication that the disposable portion of the device has expired due to expiration of the hydrogels or other issues. A detected persistent noise state may therefore result in the generation of an alert instructing the patient P to replace the disposable portion of the adherent device.

Figure 14:
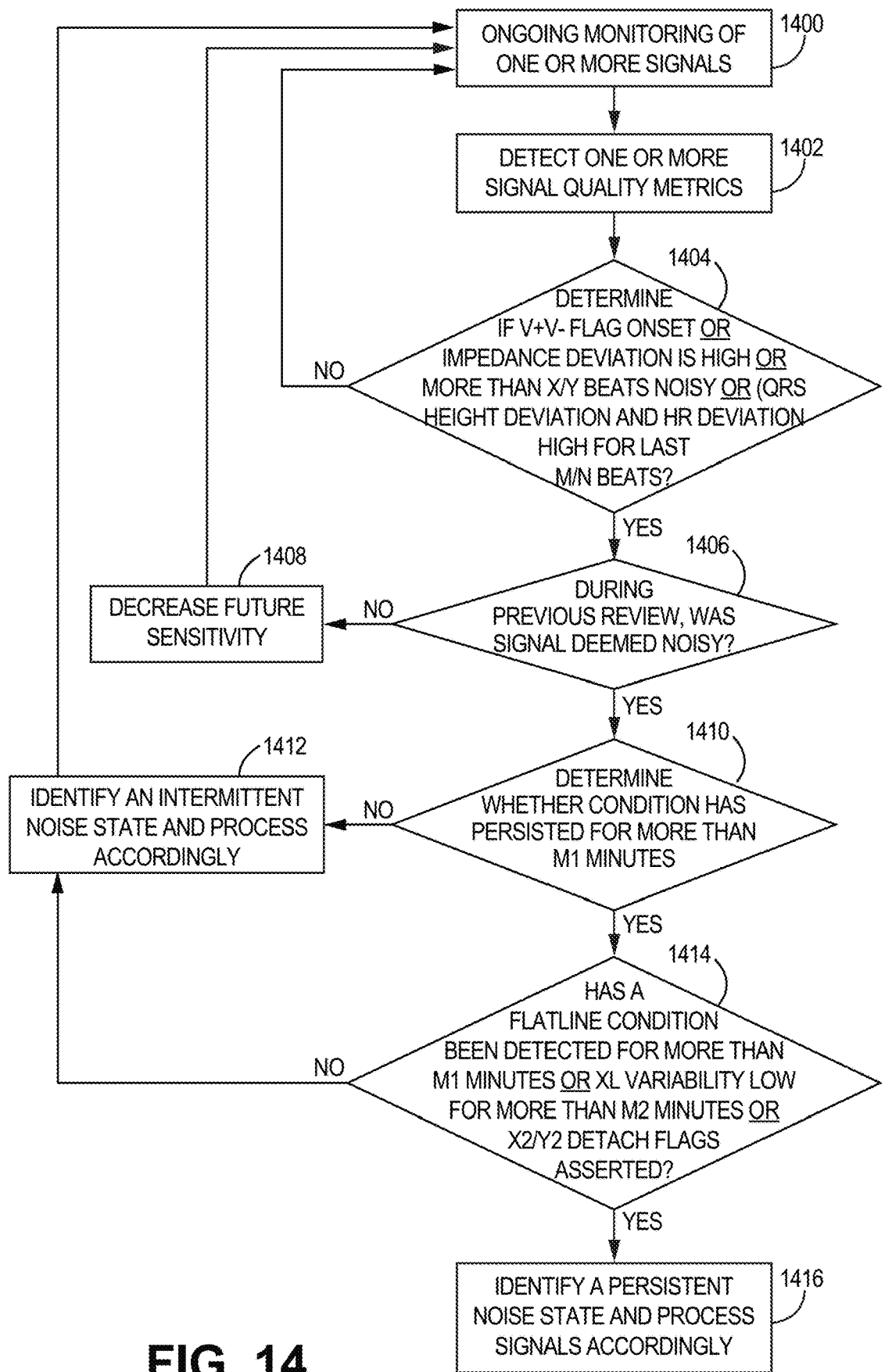
FIG. 14 is a flowchart that illustrates a method in which a combination of different signal quality metrics are combined to form a multi-parameter indicator of ECG signal noise according to some embodiments.

FIG. 14 illustrates a method in which a combination of different signal quality metrics are combined to form a multi-parameter indicator of signal noise. The method described with respect to FIG. 14 is similar to the method described with respect to FIG. 13. The main difference between the two methods is with respect to additional steps that allow for patient-specific customization of signal quality parameters. For example, after a patient adheres or otherwise affixes a new patient monitoring device (or new disposable portion of a patient monitoring device) the signal may change, resulting in changes to signal quality metrics and detection of noise conditions. In addition, signal morphology may change due to physiological changes in the patient. The embodiment provided in FIG. 14 allows for changes in the signals acquired to be incorporated into signal quality determinations.

At step 1400, one or more signals are measured in ongoing fashion. This may include ECG based signals as well as signals based on electrical design and/or other sensors. As described above, at step 1402, one or more signal quality metrics are detected and may include ECG signal-based quality measures such as beat noise flags, ECG flatline detection, deviation in QRS height and detected heart rate, as well as one or more measures based on electrical design, including V+/V− integrity checks, device detach flags, and/or bioimpedance/accelerometer measurements.

At step 1404, a combination of signal quality metrics are compared to various thresholds to detect signal quality. For example, in the embodiment shown in FIG. 14, V+/V− integrity check, bioimpedance deviation, beat noise flags. QRS height deviation, and/or HR deviation are utilized. In this embodiment, a signal quality problem is detected if one of the V+/V− integrity check is onset, the bioimpedance deviation is greater than a threshold, beat noise flag is greater than a threshold (e.g., a number X of the last Y beats have been flagged as noisy), or both QRS height deviation and heart rate (HR) deviation has been greater than a threshold for a certain number of beats (e.g., a number M of the last N beats). In this example, a combination of ECG-based signal quality metrics (beat noise flags. QRS height deviation, and HR deviation) are utilized in combination with other signal quality metrics (e.g., V+/V− integrity checks, and bioimpedance deviation) to detect signal quality issues.

If a determination is made at step 1404 that the signal is noisy, then the method proceeds to step 1406, where a determination is made whether the signal was deemed noisy during a previous review. In some embodiments, a baseline signal quality sensitivity is utilized to determine whether a signal is noisy or non-noisy, for example at step 1404. The baseline signal quality sensitivities may refer to any one of the plurality of signal quality metrics described above with respect to step 1404. At step 1406, the detection of intermittent noise at step 1404—and the sensitivity utilized to make this determination—is checked to determine if it is accurate. In some embodiments, the check may include manual review of the monitored data signals to determine if they are in fact noisy. In other embodiments, this may include using additional signal quality metrics to analyze whether the signal is in fact noisy. If review of the signal data indicates that the signal data is in fact not noisy (i.e., the signal quality metrics incorrectly identified the signal quality as poor), then at step 1408 the sensitivity of the thresholds utilized with respect to the signal quality metrics are decreases (i.e., made less sensitive). For example, if previously the noisy beat flag was set in response to three of the past ten beats being identified as noisy, then at step 1408 the sensitivity would be decreased requiring that four of the past ten beats must be identified as noisy before the beat noise flag is set (i.e., less sensitive to detecting noise). If the signal data is confirmed to have been noisy at step 1406, then no change to the sensitivity levels of the signal quality metrics is required and the method continues at steps 1410 and steps 1414 in determining whether the noise is intermittent or persistent.

At step 1410, a determination is made regarding how long the condition has persisted. In one embodiment, if the noisy signal quality condition has not persisted for longer than a threshold (e.g., M1 minutes), then at step 1412 the signal quality (for the time being) is identified as intermittently noisy and ongoing measurement continues at step 1400. If at step 1410 it is determined that the noisy signal quality condition has persisted for longer than the threshold (e.g., M1 minutes), then at step 1414 additional signal quality metrics are analyzed to confirm whether the signal quality condition is persistent or intermittent. In some embodiments, the additional signal quality metrics include one or more of flatline detection, accelerometer variability and/or detach flags. In one embodiment, a persistent signal quality noise condition is detected if at least one of signal quality metrics indicates a noise condition. For example, if the flatline metric persists for a period (e.g., T1 minutes), or accelerometer variation is low for a period (e.g., T2 minutes) or detach flags are set then the signal quality issue is identified as persistent. If none of the signal quality metrics at step 1414 indicate a persistent noise condition, then the noise condition is identified as intermittent at step 1412.

A determination at step 1410 or 1414 that the noise condition is intermittent may result in one or more actions being taken, as described above with respect to other embodiments. These include flagging/notifying downstream algorithms of the intermittent noise condition, allowing the algorithms to appropriately weight and/or de-emphasize the data analyzed, providing notifications to one or more of the patient P, the physician, the technician, or the remote monitoring center regarding the detected intermittent noise condition. Furthermore, continuing monitoring of one or more signal quality metrics and comparison to thresholds may result in a change in the noise condition status, either as an improvement indicating that the signal is (essentially) noise free or a downgrade in which the signal is determined to be persistently noisy.

At step 1416, a persistent noise condition is identified and steps are taken in response to this determination. As discussed above, identifying a persistent noise condition determines how signal data is captured and/or processed, and may differ from determinations that the noise condition is intermittent. For example, in some embodiments data recording may be halted/suspended in response to a detected persistent noise state. Similarly, flag/notifications may be set alerting downstream processing algorithms of the persistent noise condition, allowing these algorithms to properly weight or de-emphasize data signals flagged as persistently noisy. In addition, alerts may be generated requesting the user to replace the device, or to ensure that the patient is utilizing/wearing the patient monitoring device. As discussed above, persistent noise in adherent device is often-times an indication that the disposable portion of the device has expired due to expiration of the hydrogels or other issues. A detected persistent noise state may therefore result in the generation of an alert instructing the patient P to replace the disposable portion of the adherent device.

In this way, the present disclosure provides a system and method of monitoring physiological parameters of a patient and during the monitoring period, extracting a number of signal quality metrics from the monitored signals, and utilizing the signal quality metrics to determine the quality of the signal monitored (e.g., noisy or non-noisy). In this way, signal quality is determined based on the interpretability and quality of the signal being measured. This is in contrast with prior art systems, which rely only on measures of electrical contact and mechanical adhesion, which fail to ascertain whether the acquired data is of good quality.

Discussion of Possible Embodiments

The following are non-exclusive descriptions of possible embodiments of the present invention.

A method of determining signal quality in a patient monitoring device. The method may include acquiring one or more signals using the patient monitoring device. In addition, the method may include determining based on the one or more signals acquired by the patient monitoring device a first number of signal quality metrics. Noise conditions are detected based on the first number of signal quality metrics, and a determination is made whether the noise condition is intermittent or persistent. The method may further include generating an output identifying the detected noise condition and may include an indication of whether the noise condition is intermittent or persistent.

The method of the preceding paragraph can optionally include, additionally and/or alternatively any, one or more of the following features, configurations and/or additional components.

In some embodiments, the first number of signal quality metrics includes one or more of V+/V− flag onset, impedance deviation, beat noise flags, QRS height deviation, and heart rate (HR) deviation.

In some embodiments, the generated output may include one or more of a flag associated with one or more signal acquired by the patient monitoring device, an alert displayed by the patient monitoring device, and an alert displayed at a remote monitoring center.

In some embodiments, detecting a noise condition may further include comparing the first number of signal quality metrics to a first threshold level, wherein a noise condition is detected if the first number of signal quality metrics exceeds the threshold level.

In some embodiments, if a noise condition is detected, the first number of signal quality metrics is compared to a second threshold level less sensitive than the first threshold, wherein if the first number of signal quality metrics exceeds the second threshold the noise condition is identified as persistent.

In some embodiments, determining whether the noise condition is intermittent or persistent further includes determining based on the one or more signals acquired by the patient monitoring device a second number of signal quality metrics, including one or more of a flatline condition, accelerometer variation, and detach flags, wherein the second number of signal quality metrics are utilized to distinguish between intermittent noise conditions and persistent noise conditions.

In some embodiments, determining whether the noise condition should be classified as intermittent or persistent may further include monitoring a duration of the noise condition, wherein the noise condition is persistent if the duration of the noise condition exceeds a threshold value.

In some embodiments, determining whether the noise condition should be classified as intermittent or persistent may include classifying the noise condition as intermittent if the duration of the noise condition does not exceed a threshold value. In some embodiments, this step may further include determining based on the one or more signals acquired by the patient monitoring device a second number of signal quality metrics, including one or more of a flatline condition, accelerometer variation, and detach flags, wherein if the duration of the noise condition exceeds the threshold value then the second number of signal quality metrics are utilized to classify the noise condition as intermittent or persistent.

In some embodiments, the method may further include determining whether a noise condition previously detected based on the first number of signal quality metrics was correctly identified and decreasing a sensitivity level utilized to detect noise conditions if the previously identified noise condition was incorrectly identified.

In some embodiments, in response to a determination that a noise condition is persistent, an alert may be generated on the patient monitoring device indicating that the patient monitoring device has expired and needs to be replaced.

In some embodiments, in response to determination that a noise condition is intermittent, a flag may be set that identifies the one or more signals acquired by the patient monitoring device as noisy.

In another embodiment, a method of initializing a patient monitoring device at startup includes attaching a patient monitoring device to a patient. In some embodiments, the method may further include acquiring a first number of signals from the patient monitoring device, including electrocardiogram (ECG) signals, and analyzing the ECG signals to detect noisy beats. In some embodiments, detected noisy beats are utilized to determine signal quality of the first number of signals acquired by the patient monitoring device. In some embodiments, the method further includes initializing normal processing of the first number of signals acquired from the patient monitoring device if the signal quality is determined to be non-noisy.

The method of the preceding paragraph can optionally include, additionally and/or alternatively any, one or more of the following features, configurations and/or additional components.

In some embodiments, the method further includes comparing a count of detected noisy beats to a threshold value to determine signal quality.

In some embodiments, the steps of analyzing the ECG signal to detect noisy beats and utilizing the detected noisy beats to determine signal quality begin following expiration of a first duration of time following attachment of the patient monitoring device to the patient.

In some embodiments, signal quality is determined to be noisy if the detected noisy beats exceeds a threshold following expiration of a second duration of time following attachment of the patient monitoring device to the patient, wherein the second duration of time is longer than the first duration of time.

In some embodiments, the method may further include initiating a V+/V− integrity check and utilizing the V+/V− integrity check in combination with the detected noisy beats to determine signal quality.

In another embodiment, a patient monitoring device may include one or more electrodes and sensing circuitry for sensing one or more signals associated with the patient. The patient monitoring device may further include a processing module configured to receive the one or more sensed signals, wherein the processing module determines a first number of signal quality metrics based on the one or more sensed signals and detects noise conditions based on the first number of signal quality metrics and determines whether the noise condition is persistent or intermittent. The patient monitoring device may further include at least a first alert visible to a patient wearing the patient monitoring device that is activated in response to a detected noise condition.

The medical device of the preceding paragraph can optionally include, additionally and/or alternatively any, one or more of the following features, configurations and/or additional components.

In some embodiments, the patient monitoring device may further include a second alert visible to the patient wearing the patient monitoring device, wherein the first alert is activated in response to a detected persistent noise state and the second alert is activated in response to a detected intermittent noise state.

In some embodiments, the processing module may determine a second number of signal quality metrics, wherein the second number of signal quality metrics are utilized to distinguish between intermittent and persistent noise conditions.

In some embodiments, the first number of signals determined by the processor module may include one or more of V+/V− flag onset, impedance deviation, beat noise flags, QRS height deviation, and heart rate (HR) deviation, and wherein the second number of signals includes one or more of a flatline condition, accelerometer variation, and detach flags, wherein the processor module utilizes the second number of signal quality metrics are utilized to distinguish between intermittent noise conditions and persistent noise conditions.

In some embodiments, the processing module detects a noise condition by comparing the first number of signal quality metrics to a first threshold level, wherein a noise condition is detected if the first number of signal quality metrics exceeds the threshold level. In some embodiments, the processing module further determines whether the noise condition is persistent or intermittent by comparing the first number of signal quality metrics to a second threshold level less sensitive than the first threshold level, wherein if the first number of signal quality metrics exceeds the second threshold the noise condition is identified as persistent.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A patient monitoring device comprising:
   a plurality of electrodes;
   sensing circuitry for sensing an electrocardiogram (ECG) signal associated with a patient via the plurality of electrodes;
   processing circuitry configured to receive the ECG signal, wherein the processing circuitry is configured to:
      determine one or more signal quality metrics based on the ECG signal, wherein the one or more signal quality metrics include at least one beat noise flag;
      detect a noise condition based on the one or more signal quality metrics that include the at least one beat noise flag;
      classify the noise condition as intermittent or persistent based on a duration of the noise condition; and
      generate an output comprising an identifier of the noise condition and a notification of a classification of the noise condition as intermittent or persistent.

2. The patient monitoring device of claim 1, wherein to detect the noise condition, the processing circuitry is further configured to:
   detect the noise condition based on an amount of the at least one beat noise flag.

3. The patient monitoring device of claim 1, wherein to detect the noise condition, the processing circuitry is further configured to:
   detect the noise condition based on a percentage of beats having the at least one beat noise flag.

4. The patient monitoring device of claim 1, further comprising an accelerometer, wherein to classify the noise condition, the processing circuitry is further configured to:
   classify the noise condition as intermittent or persistent based on accelerometer measurements received from the accelerometer.

5. The patient monitoring device of claim 4, wherein to classify the noise condition as intermittent or persistent based on the accelerometer measurements, the processing circuitry is further configured to:

determine an amount of variation of the accelerometer measurements; and classify the noise condition as intermittent or persistent based on the amount of variation of the accelerometer measurements.

6. The patient monitoring device of claim 1, wherein the sensing circuitry is configured to make bioimpedance measurements via the electrodes, wherein to classify the noise condition, the processing circuitry is further configured to:

classify the noise condition as intermittent or persistent based on the bioimpedance measurements.

7. The patient monitoring device of claim 6, wherein to classify the noise condition as intermittent or persistent based on the bioimpedance measurements, the processing circuitry is further configured to:

determine that the bioimpedance measurements indicate bioimpedance deviation; and classify the noise condition as intermittent or persistent based on the determination that the bioimpedance measurements indicate bioimpedance deviation.

8. The patient monitoring device of claim 1, wherein the ECG signal comprises a first ECG signal, and wherein to generate the output, the processing circuitry is further configured to:

responsive to the classification of the noise condition as persistent, at least one of control the sensing circuitry to suspend collection of a second ECG signal or suspend processing of the second ECG signal; and responsive to the classification of the noise condition as intermittent, generate an output causing a downstream process to at least one of: disregard the first ECG signal, de-emphasize conclusions drawn from the first ECG signal, or weight results derived from the first ECG signal differently.

9. The patient monitoring device of claim 1, wherein the one or more signal quality metrics comprise a first one or more signal quality metrics, and the processing circuitry is further configured to:

determine a second one or more signal quality metrics; and classify the noise condition as intermittent or persistent based on the second one or more signal quality metrics.

10. The patient monitoring device of claim 9, wherein the first one or more signal quality metrics includes one or more of V+/V− flag onset, impedance deviation, QRS height deviation, or heart rate (HR) deviation, and wherein the second one or more signal quality metrics includes one or more of a flatline condition, accelerometer variation, or detach flags.

11. A method of determining signal quality in a patient monitoring device, the method comprising:

acquiring an electrocardiogram (ECG) signal using the patient monitoring device with at least one processor;

determining, based on the ECG signal acquired by the patient monitoring device, one or more signal quality metrics with the at least one processor, wherein the one or more signal quality metrics include at least one beat noise flag;

detecting, by the at least one processor, a noise condition based on the one or more signal quality metrics that include the at least one beat noise flag;

classifying, by the at least one processor, the noise condition as intermittent or persistent based on a duration of the noise condition; and generating, by the at least one processor, an output comprising an identifier of the detected noise condition and a notification of a classification of the noise condition as intermittent or persistent.

12. The method of claim 11, wherein detecting the noise condition further comprises:

detecting the noise condition based on an amount of the at least one beat noise flag.

13. The method of claim 11, wherein detecting the noise condition further comprises:

detecting the noise condition based on a percentage of beats having the at least one beat noise flag.

14. The method of claim 11, wherein classifying the noise condition further comprises:

classifying the noise condition as intermittent or persistent based on accelerometer measurements received from an accelerometer.

15. The method of claim 14 wherein classifying the noise condition as intermittent or persistent based on accelerometer measurements comprises: determining an amount of variation of the accelerometer measurements; and determining an amount of variation of the accelerometer measurements; and classifying the noise condition as intermittent or persistent based on the amount of variation of the accelerometer measurements.

16. The method of claim 11, wherein the method further comprises sensing, by sensing circuitry, bioimpedance measurements via a plurality of electrodes, wherein classifying the noise condition further comprises:

classifying the noise condition as intermittent or persistent based on the bioimpedance measurements.

17. The method of claim 16, wherein classifying the noise condition as intermittent or persistent based on the bioimpedance measurements further comprises:

determining that the bioimpedance measurements indicate bioimpedance deviation; and classifying the noise condition as intermittent or persistent based on the determination that the bioimpedance measurements indicate bioimpedance deviation.

18. The method of claim 11, wherein the ECG signal is a first ECG signal, and wherein generating the output further comprises:

responsive to the classification of the noise condition as persistent, at least one of suspending, via sensing circuitry, collection of a second ECG signal or suspending, via the sensing circuitry, processing of the second ECG signal; and responsive to the classification of the noise condition as intermittent, generating an output causing a downstream process to at least one of: disregard the first ECG signal, de-emphasize conclusions drawn from the first ECG signal, or weight results derived from the first ECG signal differently.

19. The method of claim 11, wherein the one or more signal quality metrics comprise a first one or more signal quality metrics, and the method further comprises:

determining a second one or more signal quality metrics; and classifying the noise condition as intermittent or persistent based on the second one or more signal quality metrics.

20. The method of claim 19, wherein the first one or more signal quality metrics includes one or more of V+/V− flag onset, impedance deviation, QRS height deviation, or heart rate (HR) deviation, and wherein the second one or more signal quality metrics includes one or more of a flatline condition, accelerometer variation, or detach flags.

* * * * *